(12) United States Patent
Yamashita

(10) Patent No.: US 11,617,690 B2
(45) Date of Patent: Apr. 4, 2023

(54) DISPOSABLE WEARING ARTICLE AND METHOD OF BONDING PERFORATED NONWOVEN FABRIC

(71) Applicant: Daio Paper Corporation, Ehime (JP)

(72) Inventor: Yuichi Yamashita, Ehime (JP)

(73) Assignee: Daio Paper Corporation, Ehime (JP)

( * ) Notice: Subject to any disclaimer, the term of this patent is extended or adjusted under 35 U.S.C. 154(b) by 1038 days.

(21) Appl. No.: 16/333,702

(22) PCT Filed: May 11, 2017

(86) PCT No.: PCT/JP2017/017813
§ 371 (c)(1),
(2) Date: Mar. 15, 2019

(87) PCT Pub. No.: WO2018/061289
PCT Pub. Date: Apr. 5, 2018

(65) Prior Publication Data
US 2019/0269563 A1  Sep. 5, 2019

(30) Foreign Application Priority Data

Sep. 30, 2016 (JP) .............................. JP2016-193525

(51) Int. Cl.
*A61F 13/15* (2006.01)
*A61F 13/512* (2006.01)
(Continued)

(52) U.S. Cl.
CPC ............ *A61F 13/512* (2013.01); *A61F 13/15* (2013.01); *A61F 13/15577* (2013.01);
(Continued)

(58) Field of Classification Search
CPC .. A61F 13/512; A61F 13/15; A61F 13/15577; A61F 13/49; A61F 13/496;
(Continued)

(56) References Cited

U.S. PATENT DOCUMENTS 5,658,269 A    8/1997  Osborn, III et al.
2001/0044611 A1* 11/2001  Noda ................ A61F 13/51496
                                            604/385.01
(Continued)

FOREIGN PATENT DOCUMENTS

EP    1403037    3/2004
JP    H7-501244  2/1995
(Continued)

OTHER PUBLICATIONS

Extended European Search Report for EP Application No. 17855248.5, dated Mar. 16, 2020.
(Continued)

*Primary Examiner* — Jacqueline F Stephens
(74) *Attorney, Agent, or Firm* — Andrus Intellectual Property Law

(57) ABSTRACT

To certainly fix the peripheral portion of a hole to a support sheet without losing flexibility. The above problem is solved by providing a cover nonwoven fabric in which a plurality of holes penetrating front and back surfaces at intervals, and a liquid impervious sheet in which the cover nonwoven fabric is bonded via a hot melt adhesive, in the cover nonwoven fabric, the peripheral portions of the holes are warped portion warped toward the liquid impervious sheet side, at least a tip portion of the warped portion of the cover nonwoven fabric has an adhesive portion bonded to the liquid impervious sheet via the hot melt adhesive, and a portion of the cover nonwoven fabric other than the adhesive portion is not adhered to the liquid impervious sheet.

6 Claims, 28 Drawing Sheets

(51) Int. Cl.
*A61F 13/49* (2006.01)
*A61F 13/539* (2006.01)
*A61F 13/511* (2006.01)
*A61F 13/496* (2006.01)
*A61F 13/551* (2006.01)
*A61F 13/56* (2006.01)
*A61F 13/51* (2006.01)
*A61F 13/53* (2006.01)
*A61F 13/514* (2006.01)

(52) U.S. Cl.
CPC ............ *A61F 13/49* (2013.01); *A61F 13/496* (2013.01); *A61F 13/51* (2013.01); *A61F 13/511* (2013.01); *A61F 13/514* (2013.01); *A61F 13/53* (2013.01); *A61F 13/539* (2013.01); *A61F 13/551* (2013.01); *A61F 13/56* (2013.01); *A61F 2013/15861* (2013.01); *A61F 2013/53908* (2013.01)

(58) Field of Classification Search
CPC ...... A61F 13/51; A61F 13/511; A61F 13/514; A61F 13/53; A61F 13/539; A61F 13/551; A61F 13/56; A61F 2013/15861; A61F 2013/53908
See application file for complete search history.

(56) References Cited

U.S. PATENT DOCUMENTS

| | | | |
|---|---|---|---|
| 2009/0233046 A1* | 9/2009 | Iulianetti | B32B 5/26 428/137 |
| 2010/0312209 A1 | 12/2010 | Kashiwagi | |
| 2015/0099086 A1* | 4/2015 | Kim | A61F 13/5148 428/68 |
| 2016/0075122 A1 | 3/2016 | Strube et al. | |

FOREIGN PATENT DOCUMENTS

| | | |
|---|---|---|
| JP | H9-299402 | 11/1997 |
| JP | 2002-178428 | 6/2002 |
| JP | 2005-245789 | 9/2005 |
| JP | 2009-136504 | 6/2009 |
| JP | 2011-515593 | 5/2011 |
| JP | 2015-128573 | 7/2015 |

OTHER PUBLICATIONS

International Search Report, PCT/JP2017/017813, dated Jul. 25, 2017.

* cited by examiner

FIG.11
(a)
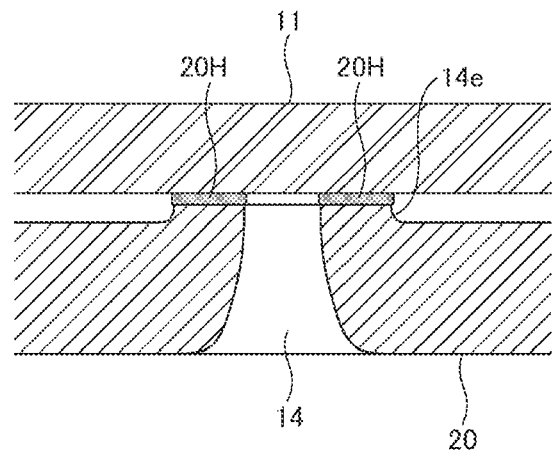
(b)
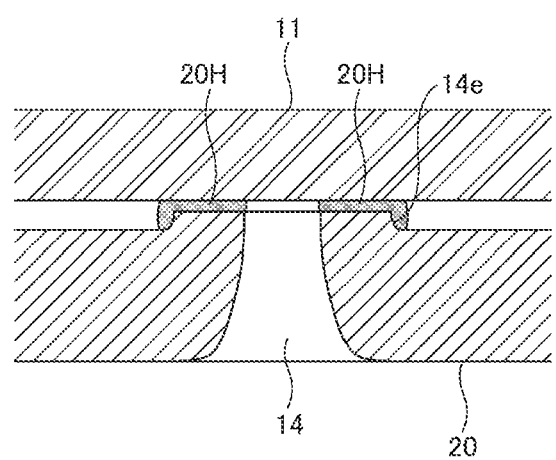
(c)
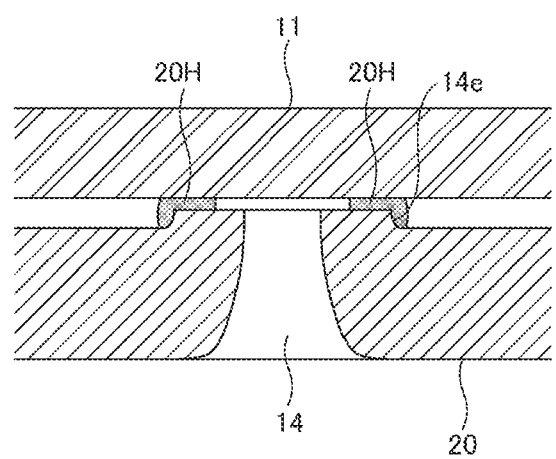

FIG.20
(a)
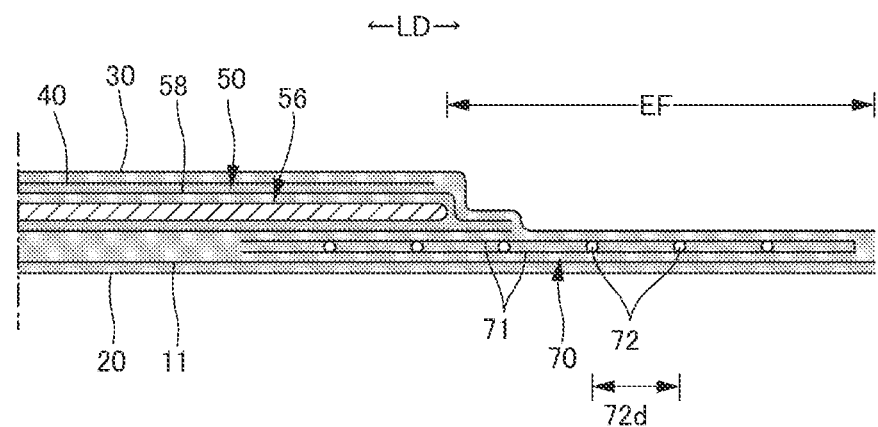
(b)
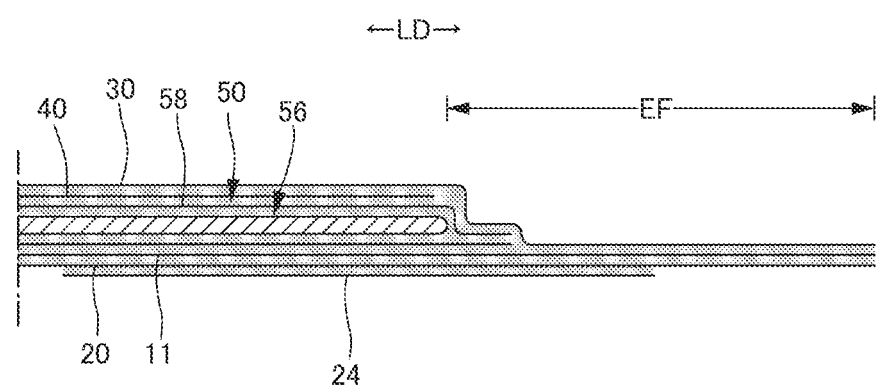
(c)
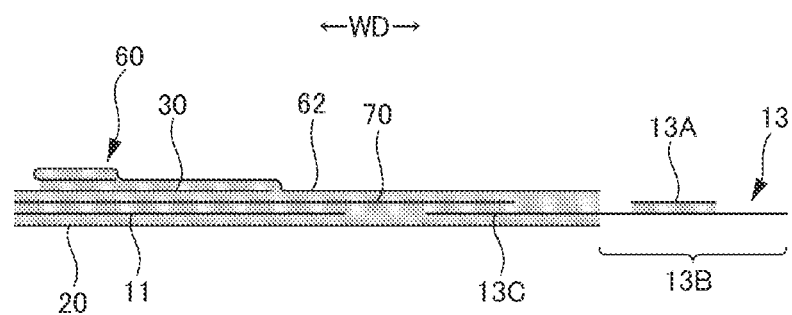

FIG.22
(a)
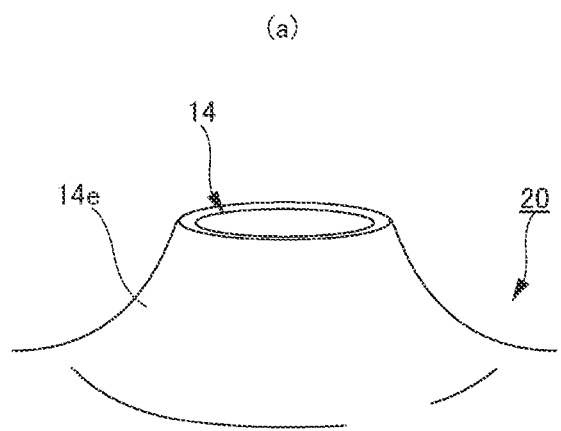
(b)
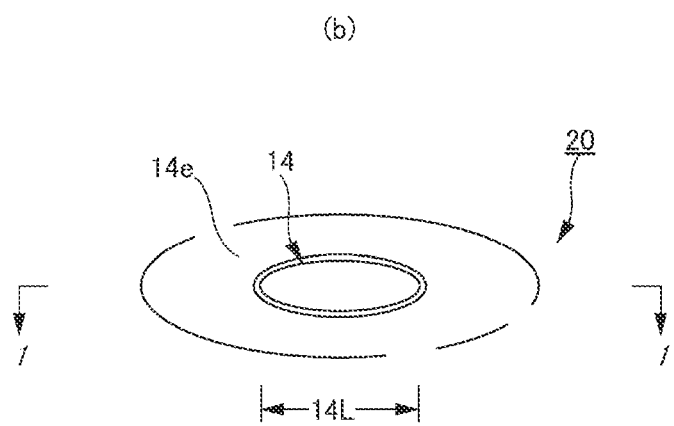
(c)
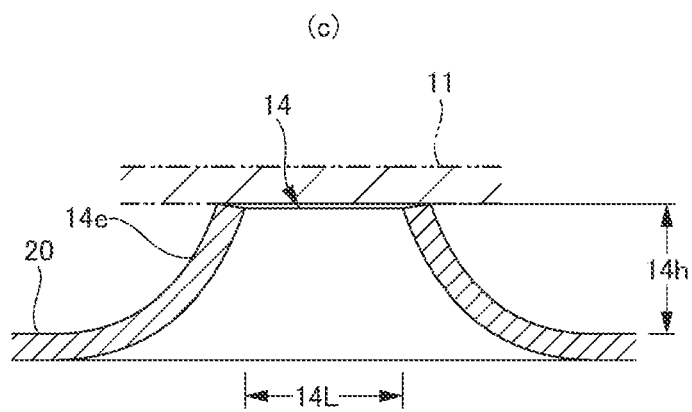

FIG.23
(a)
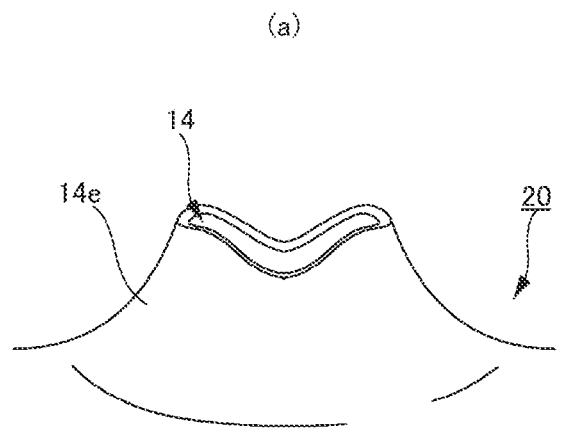
(b)
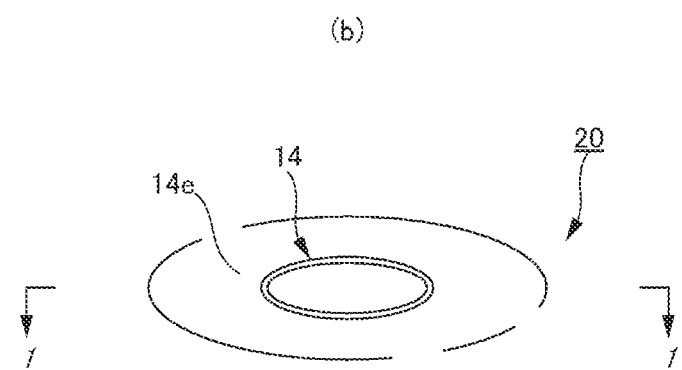
(c)
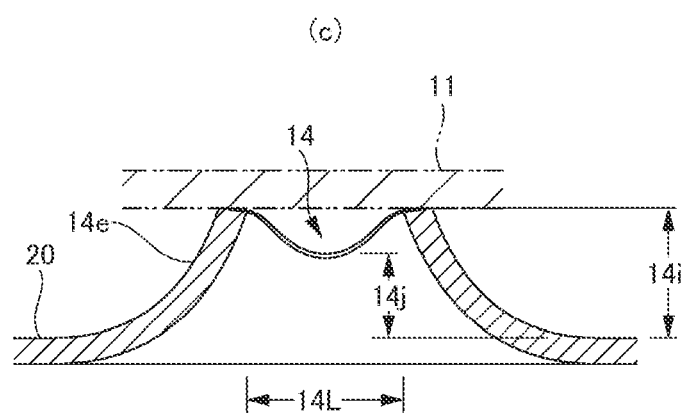

DISPOSABLE WEARING ARTICLE AND METHOD OF BONDING PERFORATED NONWOVEN FABRIC

CROSS-REFERENCE TO RELATED APPLICATIONS

This application is the U.S. national stage application of International Application PCT/JP2017/017813, filed May 11, 2017, which international application was published on Apr. 5, 2018, as International Publication WO 2018/061289 in the Japanese language. The International Application claims priority of Japanese Patent Application No. 2016-193525, filed Sep. 30, 2016. The international application and Japanese application are both incorporated herein by reference, in entirety.

TECHNICAL FIELD

The present invention relates to a disposable wearing article having a portion to which a perforated nonwoven fabric is bonded, and a method of bonding the perforated nonwoven fabric.

BACKGROUND ART

Many of disposable wearing articles such as disposable diapers and sanitary napkins are provided with a liquid impervious sheet having air permeability on the back side of an absorber in order to ensure air permeability while preventing strike-through of absorbing liquid. In addition, the back surface of the liquid impervious sheet is covered with a cover nonwoven fabric so as to have a cloth-like appearance and touch.

In this case, when the cover nonwoven fabric is stacked on the air permeable liquid impervious sheet, the air permeability lowers by the extent of the cover nonwoven fabric. One preferred method for solving this problem is to use a perforated nonwoven fabric having a large number of holes penetrating the front and back surfaces as a cover nonwoven fabric (refer to Patent Literatures 1 and 2).

However, in the case of bonding a perforated nonwoven fabric to a support sheet such as a liquid impervious sheet via a hot melt adhesive, when a hot melt adhesive is applied to positions overlapping with the holes (refer to, for example, Patent Literature 3), there is a possibility that the hot melt adhesive protrudes or is exposed to the outer surface of the perforated nonwoven fabric through the holes and adheres to manufacturing equipment, and the perforated nonwoven fabric becomes sticky. However, unless the hot-melt adhesive is applied in the vicinity of the holes, the peripheral portions of the holes are unfixed and float, and there is a possibility that the appearance or the touch deteriorates. In addition, when the hot melt adhesive is applied to a portion other than the hole, the application area of the hot melt adhesive becomes unnecessarily large, and the flexibility of the portion other than the holes may decrease.

CITATION LIST

Patent Literature

Patent Literature 1: JP 2015-128573 A
Patent Literature 2: JP 2002-178428 A
Patent Literature 3: JP 2009-136504 A

SUMMARY OF THE INVENTION

Technical Problem

Therefore, the main object of the present invention is to certainly fix the peripheral portion of a hole to a support sheet without losing the flexibility and the like.

Solution to Problem

The representative aspects of the present invention that have solved the above problems will be described below.
<First Aspect>
A disposable wearing article includes a perforated nonwoven fabric provided with a plurality of holes penetrating front and back surfaces at intervals, and a support sheet on which the perforated nonwoven fabric is bonded via a hot melt adhesive,
wherein peripheral portion of the hole in the perforated nonwoven fabric is a warped portion warped toward the support sheet side,
at least a tip portion of the warped portion of the perforated nonwoven fabric has an adhesive portion bonded to the support sheet via the hot melt adhesive, and
a portion of the perforated nonwoven fabric other than the adhesive portion is not adhered to the support sheet.
(Function and Effect)
With such a bonded structure, since the adhering area is reduced, the flexibility is not impaired, and the peripheral portion of the hole can be securely fixed to the supporting sheet. In particular, since the warped portion supports the perforated nonwoven fabric with respect to the support sheet like a pillar, the perforated nonwoven fabric becomes bulky and has excellent air permeability as compared with a nonporous nonwoven fabric having the same basis weight.
<Second Aspect>
The disposable wearing article according to the first aspect has an adhesive portion in which only a tip portion of the warped portion is bonded to the support sheet via the hot melt adhesive.
(Function and Effect)
By adhering only the tip portion of the warped portion, the flexibility is further improved while certainly fixing the edge of the hole.
<Third Aspect>
In the disposable wearing article according to the first or second aspect, an absorbent article is provided with an absorber, a liquid impervious sheet having air permeability covering a back surface side of the absorber, and a cover nonwoven fabric covering a back surface side of the liquid impervious sheet,
the cover nonwoven fabric is the perforated nonwoven fabric, and the liquid impervious sheet is the support sheet.
(Function and Effect)
It is common that an absorbent article has a cloth-like appearance by covering the back surface of an absorber with an air-permeable liquid impervious sheet and also covering its outer surface with a cover nonwoven fabric. From the viewpoint of improving air permeability, not only the air permeability of the liquid impervious sheet but also the air permeability in the thickness direction of the cover nonwoven fabric and the air permeability between the cover nonwoven fabric and the liquid impervious sheet are important. Therefore, applying the bonding structure of the perforated nonwoven fabric and the support sheet according to the present invention to the bonding structure of the cover nonwoven fabric and the liquid impervious sheet is one of the preferable forms.

<Fourth Aspect>

A method of bonding a perforated nonwoven fabric uses a pin roll having a plurality of pins arranged at intervals on a circumferential surface, a concave roll opposed to the pin roll and having concave portions into which the pins are inserted, and an adhesive application roll opposed to the pin roll on the downstream side in the rotation direction of the pin roll from the opposed position with the concave roll.

The method includes a perforation step in which a perforated nonwoven fabric is formed by passing a nonwoven fabric between the pin roll and the concave roll to pierce the pins into the nonwoven fabric and forming a large number of holes in the nonwoven fabric having a warped portion whose peripheral portion is warped to the side opposite to the pin roll side, an adhesive transfer step in which while maintaining a state in which the perforated nonwoven fabric is pierced by the pins, the perforated nonwoven fabric is guided to the adhesive application roll by the rotation of the pin roll to transfer a hot melt adhesive held on an outer peripheral surface of the adhesive application roll to at least a tip portion of the warped portion in the perforated nonwoven fabric, and a bonding step in which the perforated nonwoven fabric onto which the hot melt adhesive is transferred is separated from the pin roll with the rotation of the pin roll and then adhered by superimposing a support sheet on a surface having the hot melt adhesive.

(Function and Effect)

Such a method can manufacture a bonding structure in which at least a tip portion of the warped portion of the perforated nonwoven fabric is bonded to a support sheet via a hot melt adhesive, and a portion other than the adhesive portion of the warped portion is not adhered to the support sheet. In such a bonding structure, since the adhering area is small, the flexibility is not impaired, and the peripheral portion of a hole can be certainly fixed to the support sheet. In particular, since the warped portion supports the perforated nonwoven fabric with respect to the support sheet like a pillar, the perforated nonwoven fabric becomes bulky and has excellent air permeability as compared with a nonporous nonwoven fabric having the same basis weight.

<Fifth Aspect>

In the method of bonding a perforated nonwoven fabric according to the fourth aspect, the adhesive application roll has adhesive holding concave portions into which the pins and at least tip portions of the warped portions positioned around the pins are inserted.

In the adhesive transfer step, after holding the hot melt adhesives in the adhesive holding concave portions, the pins and at least the tip portions of the warped portions positioned around the pins are inserted into the adhesive holding concave portions, and the hot melt adhesives in the adhesive holding concave portions are applied to at least the tip portions of the warped portions of the perforated nonwoven fabric.

(Function and Effect)

With such an adhesive application roll, it is possible to reliably transfer and apply adhesives only to at least the tip portions of the warped portions in the perforated nonwoven fabric.

Advantageous Effects of Invention

As described above, according to the present invention, there is advantages such that the peripheral portion of the hole can be reliably fixed to the support sheet without impairing the air permeability and flexibility of the cover nonwoven fabric, and the like.

BRIEF DESCRIPTION OF DRAWINGS

FIG. 11 is a cross-sectional view of an adhesive portion of a cover nonwoven fabric.

FIG. 20(a) is a cross-sectional view taken along line 8-8 in FIG. 16. FIG. 20(b) is a cross-sectional view taken along line 9-9 in FIG. 16. FIG. 20(c) is a cross-sectional view taken along line 10-10 in FIG. 16.

FIG. 22(a) is a perspective view, FIG. 22(b) is a plan view, and FIG. 22(c) is a cross sectional view taken along line 1-1, illustrating holes of the cover nonwoven fabric.

FIG. 23(a) is a perspective view, FIG. 23(b) is a plan view, and FIG. 23(c) is a cross sectional view taken along line 1-1, illustrating holes of the cover nonwoven fabric.

DESCRIPTION OF EMBODIMENTS

Figure 1:
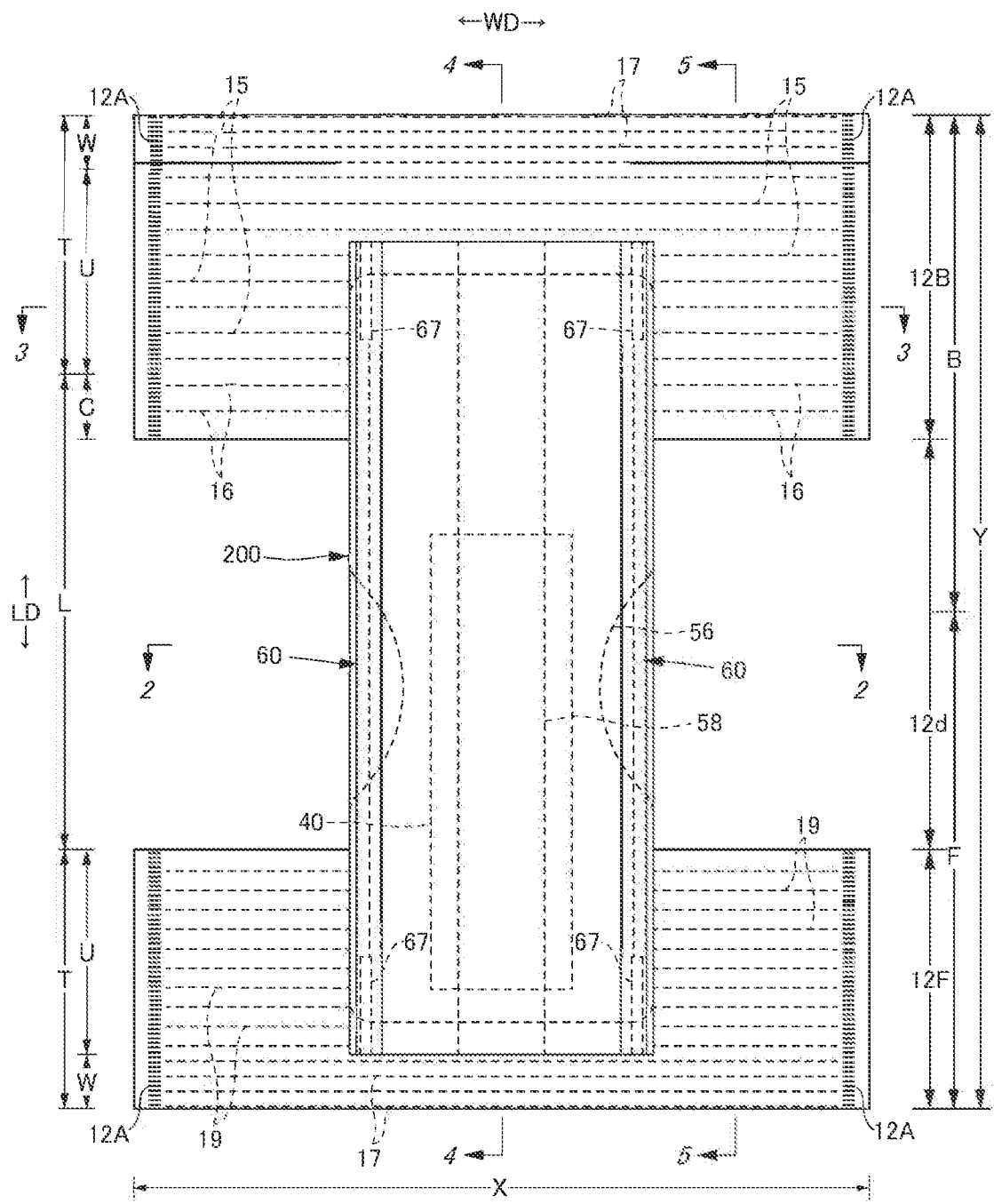
FIG. 1 is a plan view illustrating the inner surface of an underpants-type disposable diaper in a spread state.

Hereinafter, embodiments of the present invention will be described in detail with reference to the accompanying drawings. The dotted pattern portion in the cross sectional view indicates an adhesive as a bonding means for bonding respective constituent members positioned on the front surface side and the back surface side thereof, and is formed by the solid coating, bead coating, curtain coating, summit coating, or spiral coating of a hot melt adhesive, or pattern coating (transfer of the hot melt adhesive in a letterpress method). Alternatively, the fixed portion of the elastic member is formed by coating on the outer peripheral surface of an elastic member such as a comb gun or a sure wrap coating in place of or in addition to the above. Examples of the hot melt adhesive include, but are not limited to, adhesives of the EVA type, adhesive rubber type (elastomer), polyolefin, and polyester/polyamide. As a bonding means for bonding respective constituent members, a means by material welding such as heat sealing or ultrasonic sealing can also be used.

<Example of Underpants-Type Disposable Diaper>

FIGS. 1 to 7 illustrate an underpants-type disposable diaper. This underpants type disposable diaper is provided with a front outer member 12F forming a front body F and a back outer member 12B forming a back body B and an inner member 200 provided inside the outer members 12F and 12B so as to extend from the front outer member 12F to the back outer member 12B through a crotch portion. Both sides of the front outer member 12F and both sides of the back outer member 12B are joined to form a side seal portion 12A. Thus, an opening formed by the front and back end portions of the outer members 12F and 12B becomes a waist opening WO through which the torso of a wearer passes. Portions surrounded by the lower edges of the outer members 12F and 12B and the side edges of the inner member 200 on both widthwise sides of the inner member 200 serve as leg openings LO through which the legs pass. The inner member 200 is a portion for absorbing and holding excrement such as urine, and the outer members 12F and 12B are portions for supporting the inner member 200 with respect to the wearer's body. The reference sign Y denotes the maximum length of a diaper in a spread state (the length in the front-back direction from the edge of the waist opening WO of the front body F to the edge of the waist opening WO of the back body B), and the reference sign X denotes the maximum length of a diaper in a spread state.

Further, the underpants-type disposable diaper according to the present embodiment has a lower torso region T defined as a front-back direction range (a range in the front-back direction from the waist opening WO to the upper end of the leg opening LO) having the side seal portion 12A, and the intermediate region L defined as a front-back direction range of a portion forming the leg opening LO (between the region in the front-back direction having the side seal portion 12A of the front body F and the region in the front-back direction having the side seal portion 12A of the back body B). The lower torso region T can be divided into a "waist portion" W which conceptually forms an edge portion of the waist opening and an "lower waist portion" U which is a portion lower than the waist portion W. Normally, in the case of having a boundary where stretching stress of the width direction WD changes in the lower torso region T (for example, the fineness and stretch rate of the elastic member change), the waist opening WO side closest to the boundary on the waist opening WO side is the waist portion W. When there is no such boundary, the waist opening WO side of the absorber 56 or the inner member 200 is the waist portion W. The length in the front-back direction varies depending on the size of a product and can be appropriately determined. For example, the waist portion W can be set to 15 to 40 mm, and the lower waist portion U can be set to 65 to 120 mm. On the other hand, both side edges of the intermediate region L are constricted in a U shape or a curved shape along the periphery of the legs of a wearer, and this is a site for inserting the wearer's legs. As a result, the underpants-type disposable diaper in a spread state has a substantially hourglass shape as a whole.

(Inner and Outer Joined Portion)

The inner member 200 can be fixed to the outer members 12F and 12B using a bonding means by material welding such as heat sealing or ultrasonic sealing or a hot melt adhesive. In the illustrated form, the inner member 200 is fixed to the inner surface of the outer members 12F and 12B via a hot melt adhesive applied to the back surface of the inner member 200, that is, in this case, the back surface of the liquid impervious sheet 11 and the root portion 65 of the side gather 60. Inner and outer joined portions 201 for fixing the inner member 200 and the outer members 12F and 12B can be provided almost entirely in a region where those are overlapped with each other, and, for example, they can be provided in portions excluding both widthwise end portions of the inner member 200.

(Inner Member)

Figure 3:
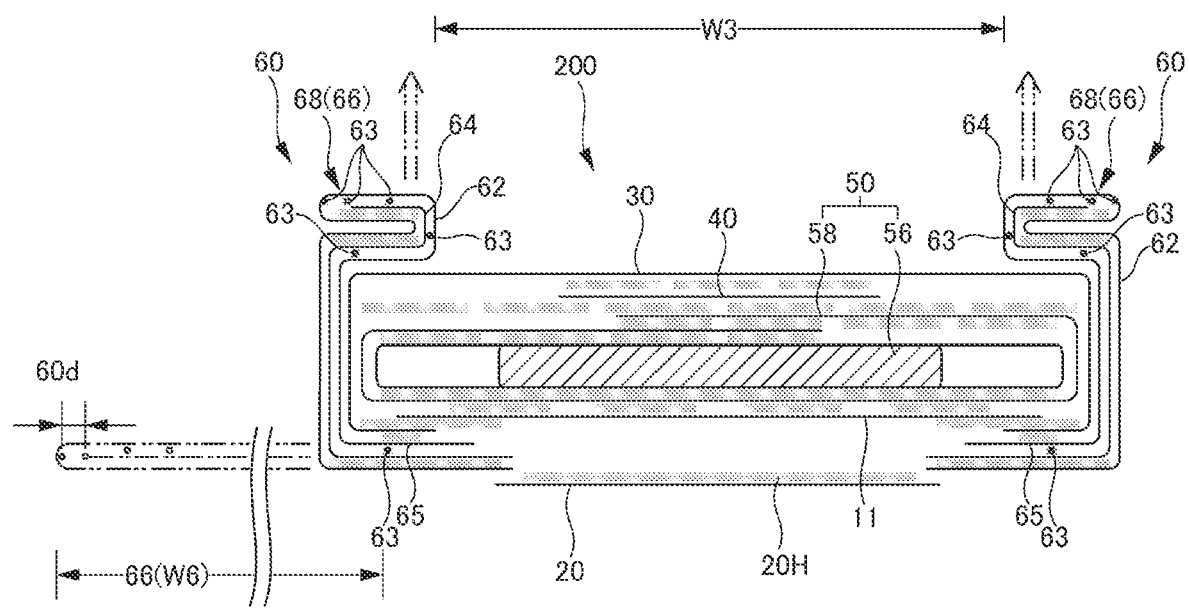
FIG. 3 is a cross-sectional view taken along line 2-2 in FIG. 1.
Figure 4:
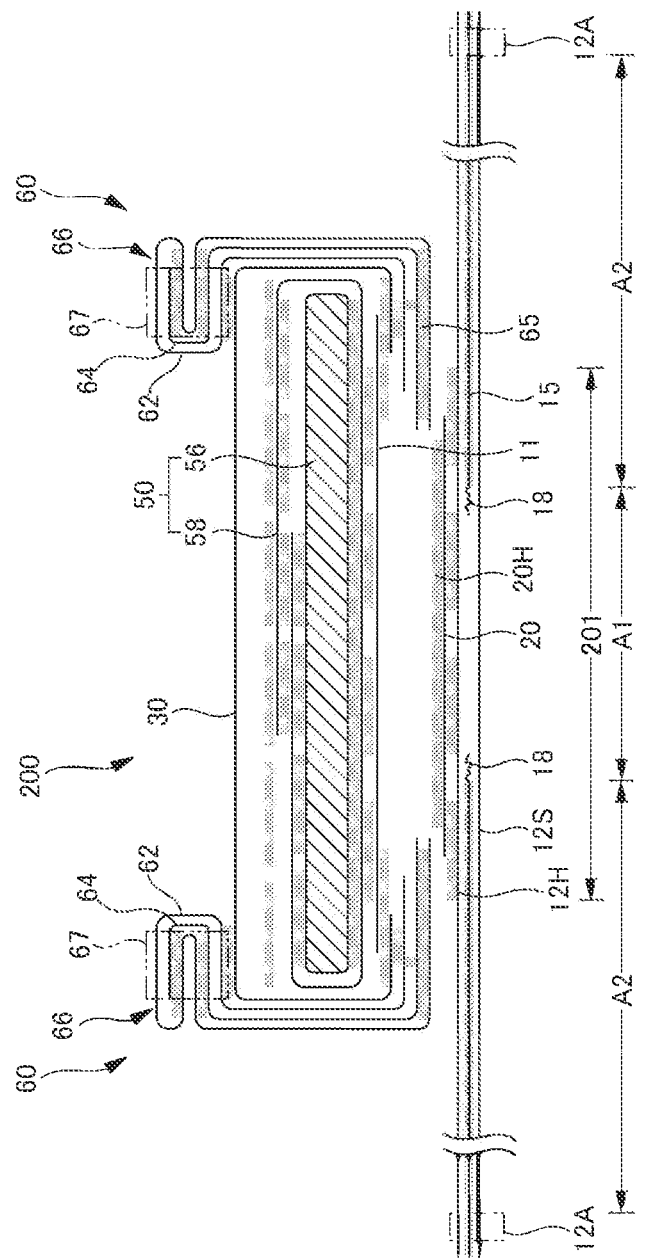
FIG. 4 is a cross-sectional view taken along line 3-3 in FIG. 1.
Figure 5:
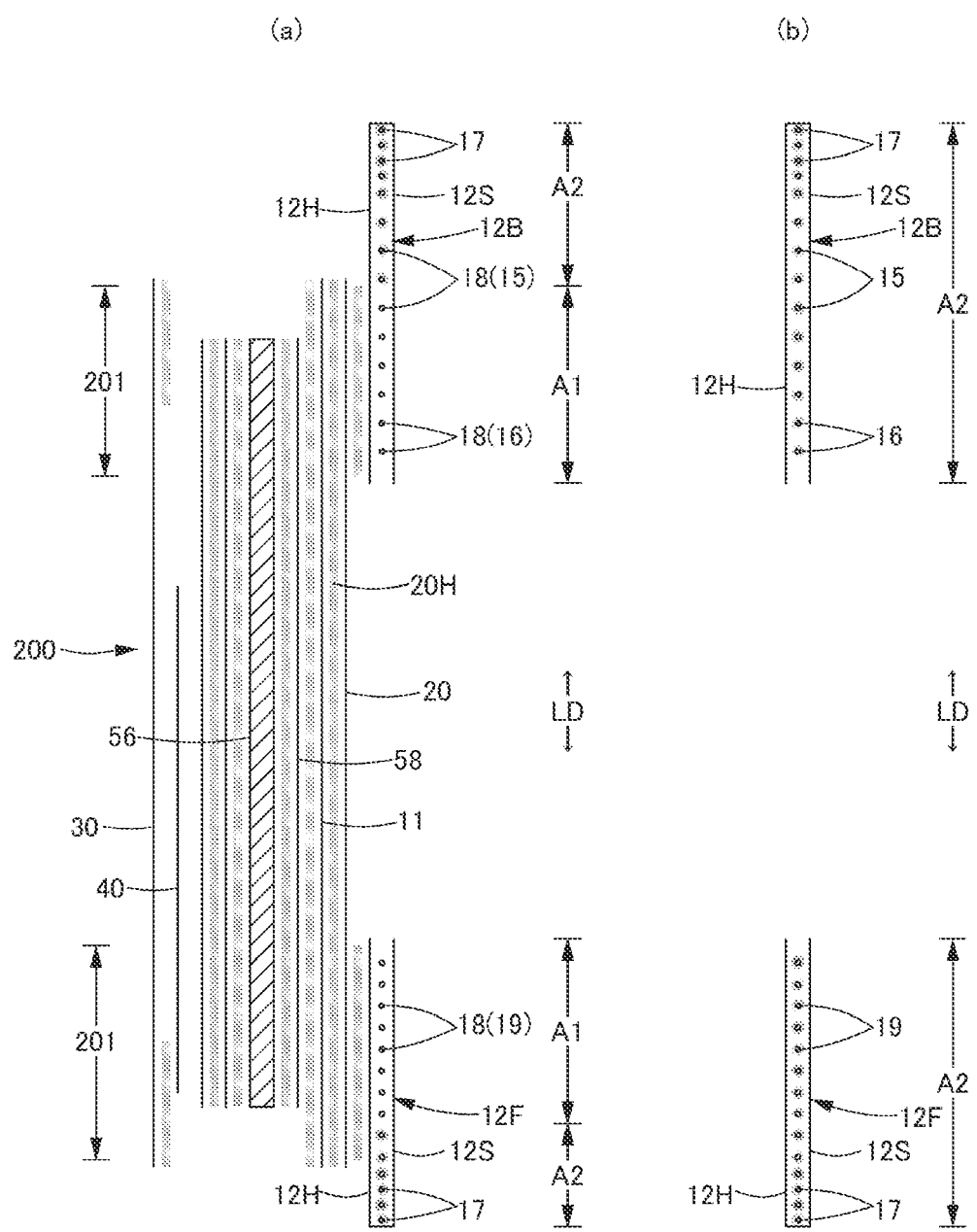
FIG. 5(a) is a cross-sectional view taken along line 4-4 in FIG. 1.
FIG. 5(b) is a cross-sectional view taken along line 5-5 in FIG. 1.
Figure 6:
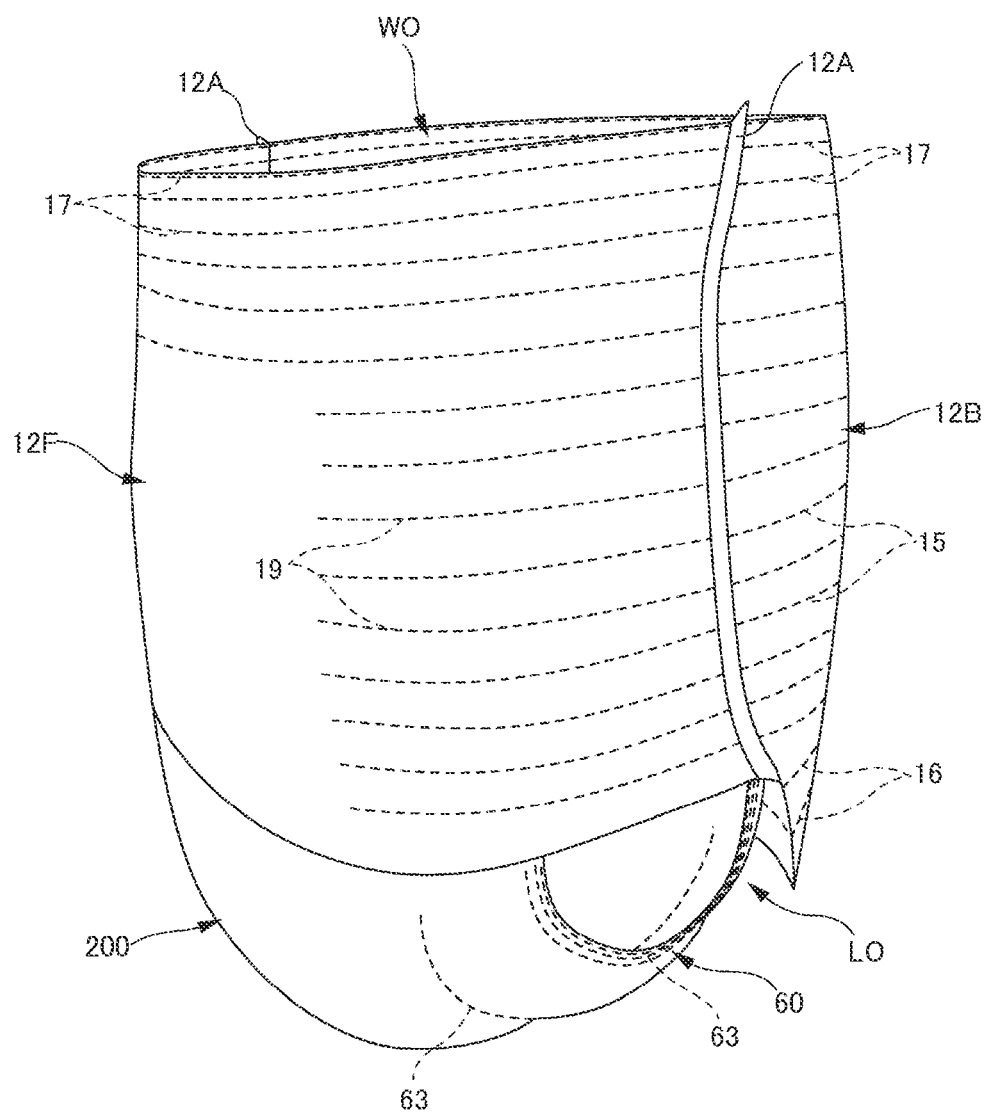
FIG. 6 is a perspective view (holes are omitted) of an underpants-type disposable diaper.

The inner member 200 can have an arbitrary shape, but in the illustrated form, it is rectangular. As illustrated in FIGS. 3 to 5, the inner member 200 is provided with a top sheet 30 which is positioned on the body side, a liquid impervious sheet 11, and an absorbent element 50 interposed therebetween, and is a main unit section that plays a role of an absorbent function. The reference sign 40 denotes an intermediate sheet (second sheet) provided between the top sheet 30 and the absorbent element 50 in order to promptly transfer liquid having permeated through the top sheet 30 to the absorbent element 50. The reference sign 60 denotes a side gather 60 extending from both sides of the inner member 200 so as to be in contact with a leg portion of a wearer in order to prevent excrement from leaking to both sides of the inner member 200.

(Top Sheet)

The top sheet 30 has a property of permeating liquid, and examples of the top sheet 30 include a perforated or non-porous nonwoven fabric and a porous plastic sheet. Among them, a raw fiber of the nonwoven fabric is not particularly limited. Examples of the raw fiber include synthetic fibers such as polyolefin such as polyethylene and polypropylene, polyester, and polyamide, regenerated fibers such as rayon and cupra, natural fibers such as cotton, mixed fibers in which two or more of these are used, and composite fibers. Further, the nonwoven fabric may be manufactured by any processing. Examples of the processing method include known methods such as a spun lace method, a spunbond method, a thermal bond method, a melt blown method, a needle punch method, an air-through method, and a point bond method. For example, if flexibility and drapeability are required, the spunbond method and the spun lace method are preferable processing methods, and if bulkiness and softness are required, the air-through method, the point bond method, and the thermal bond method are preferable processing methods.

Further, the top sheet 30 may be made of one sheet or a laminated sheet obtained by bonding two or more sheets. Similarly, the top sheet 30 may be composed of one sheet or two or more sheets with respect to the plane direction.

Both sides of the top sheet 30 may be folded back to the back side at the side edge of the absorbent element 50 or protruded laterally beyond the side edge of the absorbent element 50 without folding back.

For the purpose of preventing positional deviation with respect to the back surface side member, it is desirable that the top sheet 30 is fixed to a member adjacent to the back surface side by a bonding means by material welding such as heat sealing or ultrasonic sealing or a hot melt adhesive. In the illustrated form, the top sheet 30 is fixed to the surface of the intermediate sheet 40 and the surface of the package sheet 58, which is located on the front surface side of the absorber 56, by a hot melt adhesive applied on the back surface thereof.

(Intermediate Sheet)

To quickly transfer liquid having permeated through the top sheet 30 to the absorber, it is possible to provide an intermediate sheet (also referred to as a "second sheet") 40 having a higher liquid permeation rate than the top sheet 30. This intermediate sheet 40 not only improves the absorption performance by an absorber by immediately moving liquid to the absorber, but also prevents the absorbent liquid from returning from the absorber and makes the surface of the top sheet 30 constantly dry. The intermediate sheet 40 can also be omitted.

Examples of the intermediate sheet 40 include the same material as the top sheet 30, a spun lace, a spunbond, SMS, a pulp nonwoven fabric, a mixed sheet of pulp and rayon, a point bond, or a crepe paper. In particular, an air-through nonwoven fabric is preferable because it is bulky. It is preferable to use a composite fiber having a core-sheath structure for the air-through nonwoven fabric. In this case, resin used for the core may be polypropylene (PP), but polyester (PET) having high rigidity is preferable. The basis weight is preferably 20 to 80 g/m$^2$, more preferably 25 to 60 g/m$^2$. The fineness of the raw fiber of the nonwoven fabric is preferably 2.0 to 10 dtex. To increase the bulkiness of the nonwoven fabric, it is also preferable to use eccentric fibers, whose core is not in the center, hollow fibers, eccentric and hollow fibers, as mixed fibers of all or a part of the raw material fibers.

The intermediate sheet 40 in the illustrated form is disposed at the center shorter than the width of the absorber 56, but may be provided over the range covering the maximum width. The length of the intermediate sheet 40 in the longitudinal direction may be the same as the maximum length of a diaper, may be the same as the length of the absorbent element 50, or may be within a short length range around a region receiving a liquid.

For the purpose of preventing positional deviation with respect to the back surface side member, it is desirable that the intermediate sheet 40 be fixed to a member adjacent to the back surface side by a bonding means by material welding such as heat sealing and ultrasonic sealing, or a hot melt adhesive. In the illustrated form, the intermediate sheet 40 is fixed to the surface of the package sheet 58, which is located on the front surface side of the absorber 56, by a hot melt adhesive applied on the back surface thereof.

(Liquid Impervious Sheet)

The material of the liquid impervious sheet 11 is not particularly limited, but examples of the material include a plastic film made of a polyolefin resin such as polyethylene and polypropylene, a laminated nonwoven fabric having a plastic film on the surface of a nonwoven fabric, and a laminated sheet obtained by bonding nonwoven fabrics or the like on a plastic film. In the liquid impervious sheet 11, it is preferable to use a material having liquid impermeability and moisture permeability that has been favorably used from the viewpoint of prevention of stuffiness. As the moisture-permeable plastic film, a microporous plastic film is widely used. The microporous plastic film is obtained by stretching a sheet in a monoaxial or biaxial direction after forming the sheet by kneading an inorganic filler and a polyolefin-based resin such as polyethylene or polypropylene. In addition to this, a nonwoven fabric using a micro-denier fiber and a liquid impervious sheet without a plastic film, in which leakage resistance is increased by reducing gaps of fiber by applying heat and pressure and by coating with highly water-absorbing resin, a hydrophobic resin, or a water repellent agent, can also be used as the liquid impervious sheet 11. However, it is desirable to use a plastic film to obtain sufficient adhesive strength in the case of adhering to the cover nonwoven fabric 20 to be described later via a hot melt adhesive.

To enhance leakage resistance, the liquid impervious sheet 11 may have a width such that it fits on the back surface side of the absorbent element 50 as illustrated in the drawing and can also be disposed around the both sides of the absorbent element 50 to extend to the both sides of the side surface of the top sheet 30 of the absorbent element 50. It is appropriate that the width of this extending portion is about 5 to 20 mm on each side.

Further, on the inside of the liquid impervious sheet 11, in particular, on the side surface of the absorber 56, an excretion indicator that changes its color due to absorption of a liquid component can be provided.

(Side Gather)

The side gathers 60 extend along the both sides of the inner member 200 in the front-back direction LD and are provided so as to contact the wearer's legs to prevent side leakage, and in general, examples of the side gathers 60 include gathers called a three-dimensional gather and a planar gather.

The side gathers 60 of the first embodiment illustrated in FIGS. 3 and 4 are so-called three-dimensional gathers and stand upright from the side portion of the inner member 200 to the front surface side. In the side gathers 60, the root-side portion stands diagonally toward the center in the width direction, and the portion closer to the tip side from the intermediate portion stands diagonally outward in the width direction, but this is not limited thereto, and it can be appropriately changed to a form of standing on the center side in the width direction as a whole or the like.

To be more specific, the side gather 60 according to the first embodiment is formed by folding back in two, in the width direction WD at a portion to be a tip portion, a belt shaped gather nonwoven fabric 62 having a length equal to the length in the front-back direction of the inner member 200, and fixing a plurality of elongated gather elastic members 63 with intervals in the width direction WD in an extended state along the longitudinal direction between the folded back portion and an adjacent sheet. A base portion (an end portion on the side opposite to the sheet folded back portion in the width direction WD) positioned on the opposite side of the tip portion of the side gathers 60 is the root portion 65 fixed to the side portion on the back surface side of the liquid impervious sheet 11 in the inner member 200, and portions other than the root portion 65 are a main unit portion 66 (a portion on the folded back portion side) extending from the root portion 65. The main unit portion 66 is composed of a root side portion directed toward the center in the width direction and a tip side portion folded back outward in the width direction from the tip of the root side portion. Although this embodiment is a surface contact type side gather 60, a line contact type side gather 60 which is not folded back outward in the width direction can also be used. Both end portions of the main unit portion 66 in the front-back direction are set to be fallen portions 67 fixed to the side surface of the top sheet 30 in a fallen state, while the intermediate portion in the front-back direction positioned therebetween is an non-fixed free portion 68, and the gather elastic member 63 along the front-back direction LD is fixed to the free portion 68 in a stretched state.

As the gather nonwoven fabric 62, a nonwoven fabric which is flexible and excellent in uniformity and concealing property such as a spunbonded nonwoven fabric (SS, SSS, etc.), SMS nonwoven fabric (SMS, SSMMS, etc.), melt-blown nonwoven fabric, and on which a water repellent process is performed by silicon as necessary, can be preferably used, and the fiber basis weight is preferably set to about 10 to 30 g/m$^2$. As the gather elastic member 63, a rubber thread or the like can be used. When a spandex rubber thread is used, the fineness is preferably 470 to 1240 dtex, more preferably 620 to 940 dtex. The stretch rate at the time of fixing is preferably from 150 to 350%, more preferably from 200 to 300%. The term "stretch rate" means a value when the natural length is taken as 100%. As illustrated in the drawing, a waterproof film 64 may be interposed between the gather nonwoven fabrics 62 folded in two, and in this case, the gather nonwoven fabric 62 may be partially omitted in the portion where the waterproof film 64 is present. However, in order to make the appearance and feel of the product like a cloth, it is necessary that at least the outer surface from the base end to the tip of the side gathers 60 is formed of the gather nonwoven fabric 62 as the illustrated embodiment.

The number of the elongated gather elastic members 63 provided in the free portion of the side gather 60 is preferably two to six, more preferably three to five. An appropriate arrangement interval 60d is 3 to 10 mm With such a configuration, a range in which the gather elastic member 63 is disposed easily comes into surface contact with the skin. The gather elastic member 63 may be disposed not only on the tip side but also on the root side.

In the free portion 68 of the side gathers 60, at least one of hot melt adhesives to be applied by various application methods and a fixing means using material welding such as a heat sealing, ultrasonic sealing, and the like can be used for bonding the inner layer and the outer layer of the gather nonwoven fabric 62 and fixing the gather elastic member 63 sandwiched therebetween. When the inner layer and the outer layer of the gather nonwoven fabric 62 are entirely bonded together, the flexibility is impaired. Therefore, it is preferable that the portion other than the adhesive portion of the gather elastic member 63 is not adhered or is weakly adhered. In the illustrated embodiment, by applying a hot melt adhesive only to the outer peripheral surface of the gather elastic member 63 by an application means such as a comb gun or a sure wrap nozzle and sandwiching it between the inner layer and the outer layer of the gather nonwoven fabric 62, fixing of the elongated gather elastic member to the inner layer and the outer layer of the gather nonwoven fabric 62 and fixing between the inner layer and the outer layer of the gather nonwoven fabric 62 are carried out by using only the hot melt adhesive applied to the outer peripheral surface of the gather elastic member 63.

Further, at least one of a hot melt adhesive to be applied by various application methods and a means using material welding such as a heat sealing, ultrasonic sealing and the like can be used for fixing the waterproof film 64 built in the side gather 60 and the gather nonwoven fabric 62 and fixing the fallen portion 67 to the side surface of the inner member 200. In the illustrated embodiment, slot application of a hot melt adhesive is used for fixing the waterproof film 64. In addition, in order to fix the fallen portion 67 in the illustrated embodiment, the hot melt adhesive and the means by material welding are used in combination, but these fixing can be carried out only by any one of them.

The fixing target of the root portion 65 of the side gather 60 can be an appropriate member such as the top sheet 30, the liquid impervious sheet 11, and the absorbent element 50 in the inner member 200.

In the side gather 60 formed as described above, according to the first embodiment, a contraction force of the gather elastic member 63 acts so as to bring both ends in the front-back direction close to each other. Though both ends in the front-back direction of the main unit portion 66 are fixed in a fallen state, a space between the both ends is a non-fixed free portion. Therefore, only the free portion stands so as to come into contact with the body side as indicated by the arrows of FIG. 3. Particularly, when the root portion 65 is positioned on the back surface side of the inner member 200, the side gathers 60 stand up so as to open outward in the width direction at and around a crotch portion, such that the side gathers 60 come into surface contact with a leg portion, and therefore the fitness is improved.

Figure 12:
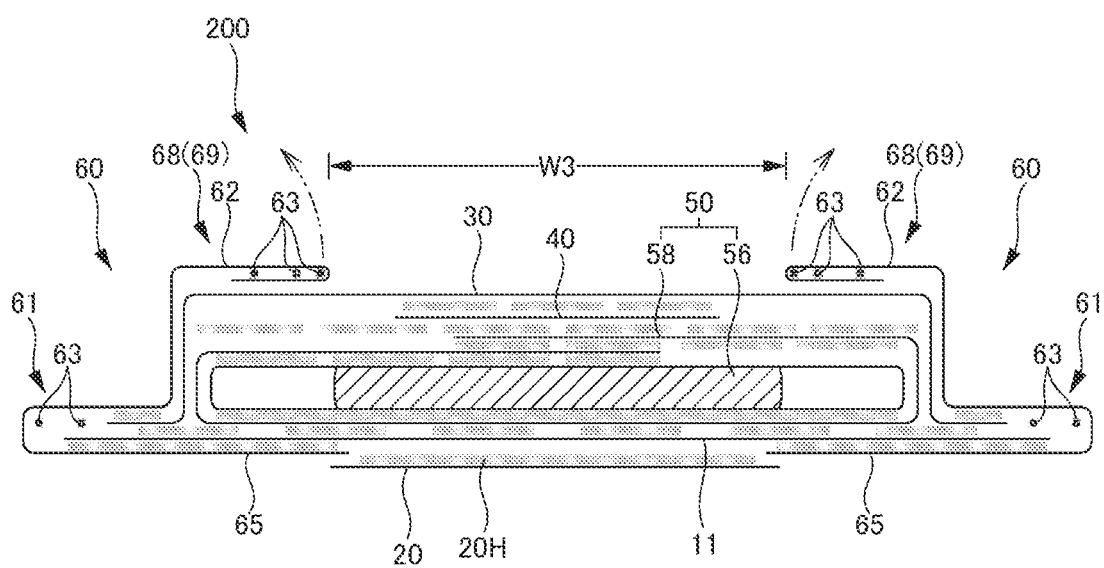
FIG. 12 is a cross-sectional view taken along line 2-2 in FIG. 1, illustrating another embodiment.
Figure 13:
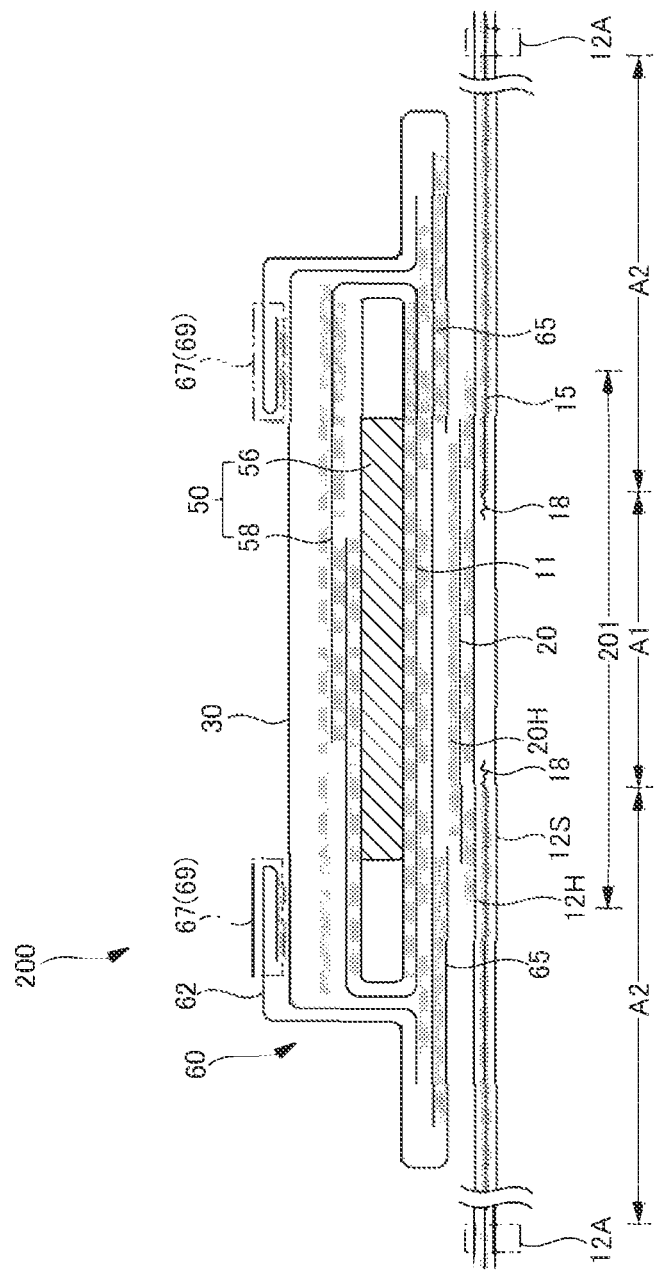
FIG. 13 is a cross-sectional view taken along line 3-3 in FIG. 1, illustrating another embodiment.

Although the dimension of the side gather 60 of the first embodiment is appropriately determined, in the case of an infant disposable diaper, as illustrated in FIG. 3, for example, the standing height of the side gathers 60 (widthwise length of the main unit portion 66 in the spread state) W6 is preferably 15 to 60 mm, in particular 20 to 40 mm. Further, in a state where the side gathers 60 are folded flat so as to be parallel to the surface of the top sheet 30, the distance W3 between the innermost folds is preferably from 60 to 190 mm, in particular from 70 to 140 mm Although the side gathers 60 of the first embodiment include only the three-dimensional gathers, they may include both three-dimensional gathers and planar gathers or may include only planar gathers. FIGS. 12 and 13 illustrate the side gather 60 according to the second embodiment including both three-dimensional gathers and planar gathers. Each of the side gathers 60 includes from the root portion 65 fixed to a side portion on the back surface side of the liquid impervious sheet 11 in the inner member 200 to a first portion 61 (planar gather portion) protruding to the side of the inner member 200 and includes from the root portions 65 fixed to both sides of the top sheet 30 of the inner member 200 to a second portion 69 (three-dimensional gather portion) protruding to the front surface side of the inner member 200. More specifically, a belt shaped gather nonwoven fabric 62 having a length equal to the length in the front-back direction of the inner member 200 extends laterally from the root portion 65 and is folded back to the front surface side at the tip of the first portion 61, and the portion folded on the front surface side reaches the second portion 69 via the first portion 61 and is folded back at the tip of the second portion 69. In the folded portion of the gather nonwoven fabric 62, facing portions are joined by a hot melt adhesive or the like.

Both end portions in the front-back direction of the second portion 69 are formed as the fallen portion 67 fixed to the side surface of the top sheet 30 in a fallen state. On the other hand, the intermediate portion in the front-back direction positioned therebetween is a non-fixed free portion 68. At least in the front-back direction intermediate portion of the first portion 61 and in the free portion 68 of the second portion 69, one gather elastic member 63 along the front-back direction LD is fixed in a stretched state, or a plurality of the gather elastic members 63 is fixed in a stretched state at intervals in the width direction WD, and the free portion 68 of the second portion 69 contracts in the front-back direction LD due to its contraction force and becomes a three-dimensional gather in contact with a leg portion. Further, the first portion 61 contracts in the front-back direction LD and becomes a planner gather in contact with the leg portion.

Other points relating to the second embodiment, for example, the material of the gather nonwoven fabric 62, the material of the gather elastic member 63, and the like are the same as those in the first embodiment, and therefore the description is omitted.

(Absorbent Element)

The absorbent element 50 has the absorber 56 and a package sheet 58 packaging the entire absorber 56. The package sheet 58 can also be omitted.

(Absorber)

The absorber 56 can be formed of an assembly of fibers. As this fiber assembly, besides those obtained by stacking short fibers such as fluff pulp and synthetic fibers, a filament assembly obtained by opening tows (fiber bundles) of synthetic fibers such as cellulose acetate as required can also be used. When fluff pulp or short fibers are stacked, fiber basis weight can be set to, for example, about 100 to 300 g/m², and in the case of a filament assembly, fiber basis weight can be set to about 30 to 120 g/m². In the case of a synthetic fiber, the fineness is, for example, 1 to 16 dtex, preferably 1 to 10 dtex, more preferably 1 to 5 dtex. In the case of filament assembly, the filaments may be non-crimped fibers, but are preferably crimped fibers. The degree of crimp of the crimped fiber can be, for example, about 5 to 75, preferably 10 to 50, and more preferably about 15 to 50 per inch. In addition, crimped fibers which are uniformly crimped are often used. It is preferable to disperse and hold the high absorbent polymer particles in the absorber 56.

Figure 7:
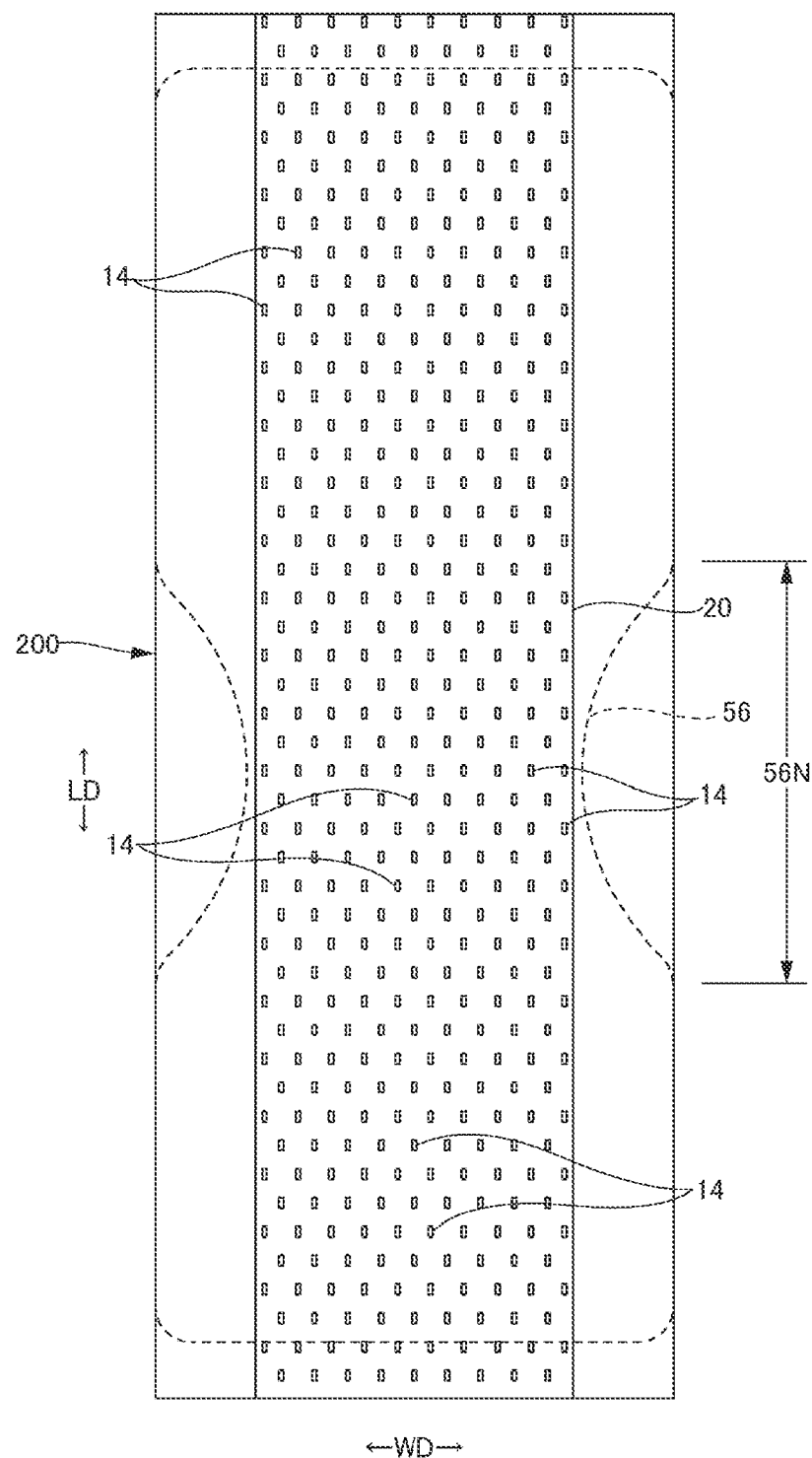
FIG. 7 is a plan view illustrating the outer surface of an inner member in a spread state.

The absorber 56 may have a rectangular shape, and, as illustrated in FIGS. 1 and 7, preferably has an hourglass-shape having the front end portion, the back end portion, and a constricted portion 56N positioned between the front end portion and the back end portion and having narrower width than that of the front end portion and the back end portion, since the fitness of the absorber 56 itself and the side gather 60 around the legs is improved.

The dimension of the absorber 56 can be appropriately determined as far as it extends over the front, back, right and left of the position of a ureteral outlet, but it is preferable that it extends to the peripheral portion of the inner member 200 or the vicinity thereof in the front-back direction LD and the width direction WD. The reference sign 56X denotes the width of the absorber 56.

(High Absorbent Polymer Particle)

The absorber 56 can contain high absorbent polymer particles partially or entirely. The high absorbent polymer particles mean "powder" in addition to "particles". The high-absorbent polymer particles 54 used for this type of disposable diapers can be used as they are, and it is desirable that the proportion of particles remaining on a sieve is less than 30% by weight by sieving (shaking for 5 minutes) using, for example, a standard sieve of 500 μm (JIS Z 8801-1: 2006). In addition, it is desirable that the proportion of particles remaining on the sieve by sieving (shaking for 5 minutes) using a standard sieve of 180 μm (JIS Z 8801-1: 2006) be 60% by weight or more.

The material of the high absorbent polymer particles is not particularly limited, but materials having a water absorption of 40 g/g or more are suitable. Examples of the high absorbent polymer particles include starch-based, cellulose-based, and synthetic polymer-based particles, and starch-acrylic acid (salt) graft copolymers, saponified starch-acrylonitrile copolymers, crosslinked sodium carboxymethylcellulose, and acrylic acid (salt) polymers can be used. As the shape of the high absorbent polymer particles, powder and granular particles which are usually used are preferable, but other shapes can also be used.

The superabsorbent polymer particles having a water absorption rate of 70 seconds or less, particularly 40 seconds or less, are suitably used. If the water absorption rate is too slow, back-flow, in which the liquid fed into the absorber 56 returns to the outside of the absorber 56, is likely to occur.

As the high absorbent polymer particles, those having a gel strength of 1,000 Pa or more are preferably used. Thereby, even when the absorber 56 is bulky, it is possible to effectively suppress stickiness after liquid absorption.

The basis weight of the high-absorbent polymer particles can be appropriately determined according to the absorption amount required for the use of the absorber 56. Therefore, although it cannot be said unconditionally, the basis weight can be 50 to 350 g/m². When the basis weight of the polymer is less than 50 g/m², it is difficult to ensure the absorption amount. When it exceeds 350 g/m², the effect is saturated.

If necessary, a spraying density or a spraying amount of the high absorbent polymer particles can be adjusted in the planar direction of the absorber 56. For example, it is possible to increase the spraying amount in an excretory site of liquid compared to the other sites. When considering the difference between men and women, it is possible to increase the spray density (amount) on the front side for men and to increase the spray density (amount) at the center for women. Further, a portion without polymer can be provided locally (for example, in a spot shape) in the planar direction of the absorber 56.

(Package Sheet)

When the package sheet 58 is used, tissue paper, particularly crepe paper, a nonwoven fabric, a poly lamina nonwoven fabric, a sheet with small openings can be used as the material. However, it is desirable that the sheet from which the high absorbent polymer particles do not come off is used. When a nonwoven fabric is used in place of crepe paper, a hydrophilic SMS nonwoven fabric (SMS, SSMMS, etc.) is particularly suitable, and polypropylene, polyethylene/polypropylene composite material and the like can be used as the material. It is desirable that the basis weight is 5 to 40 g/m², particularly 10 to 30 g/m².

The packaging form of the package sheet 58 can be appropriately determined. However, from the viewpoints of ease of manufacturing and prevention of leakage of highly absorbent polymer particles from the front and back end edges, it is preferable that the package sheet 58 is wound around in a cylindrical shape so as to surround the front and back surfaces and both side surfaces of the absorber 56, the front and back edge portions are protruded from the front and back of the absorber 56, and the wound and overlapping portion and the overlapping portion of the front-back protruding portions are joined by means such as hot melt adhesive, material welding, or the like.

(Outer Member)

Figure 14:
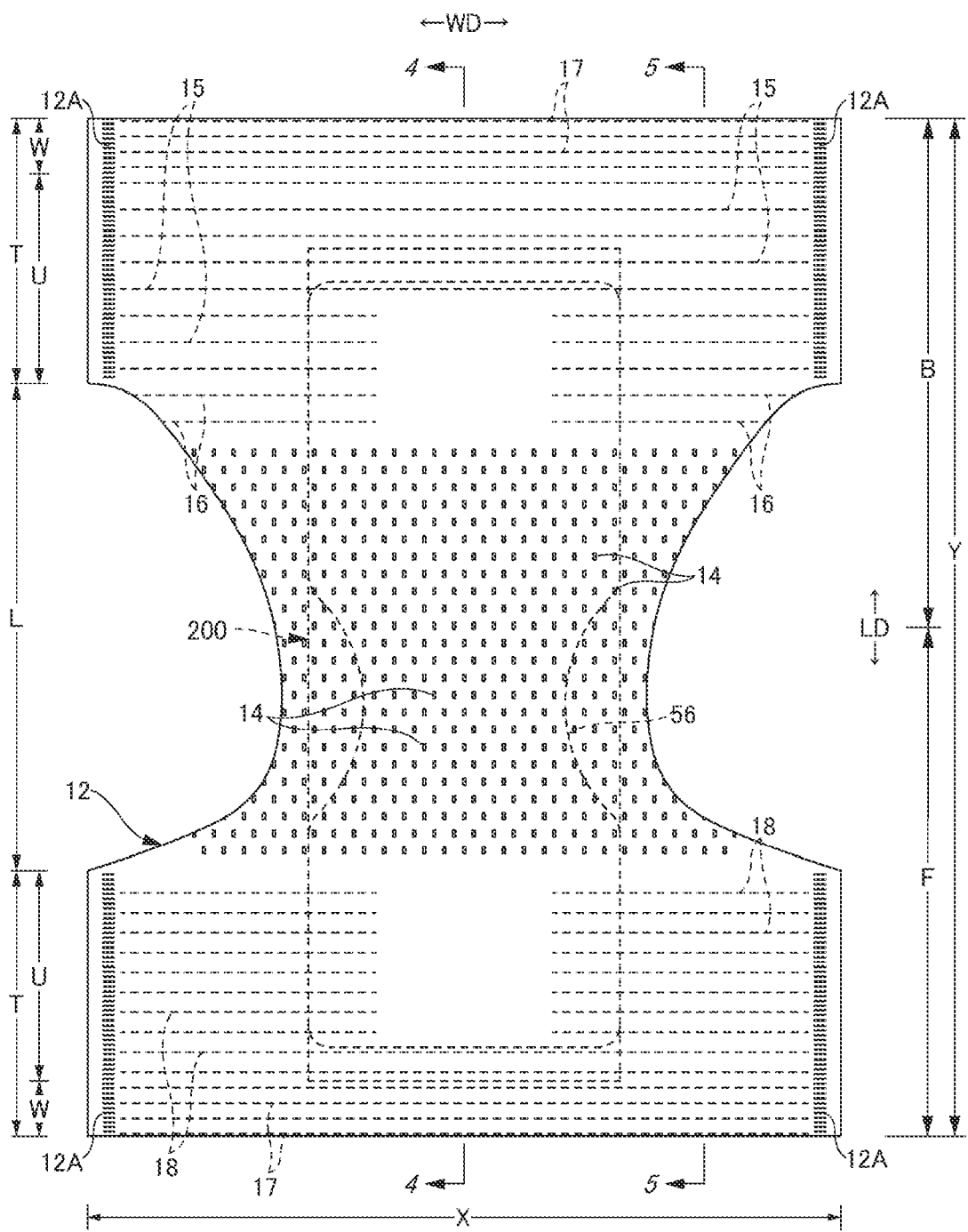
FIG. 14 is a plan view illustrating the outer surface of an underpants-type disposable diaper in a spread state.
Figure 15:
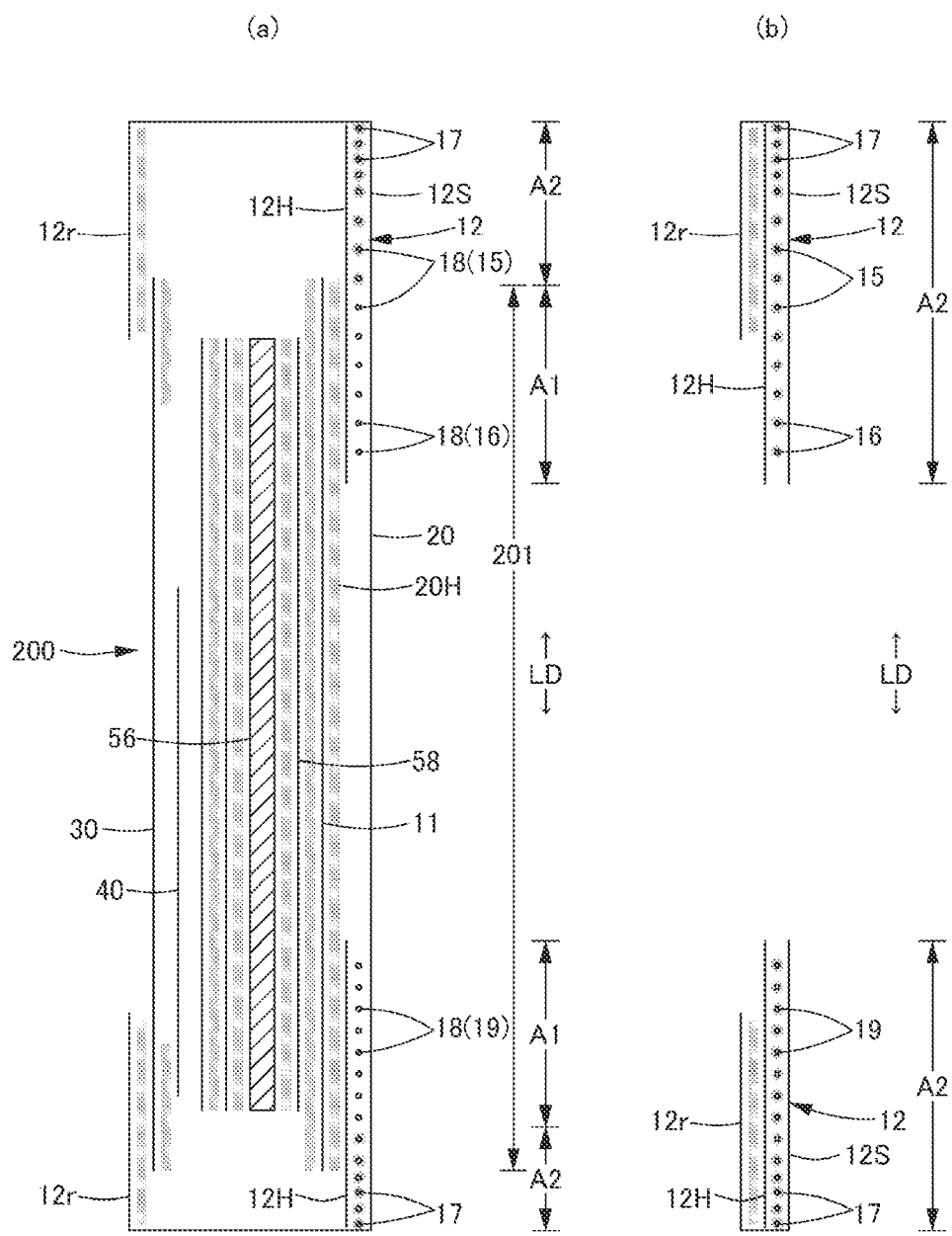
FIG. 15(a) is a cross-sectional view taken along line 4-4 in FIG. 14.
FIG. 15(b) is a cross-sectional view taken along line 5-5 in FIG. 14.
Figure 16:
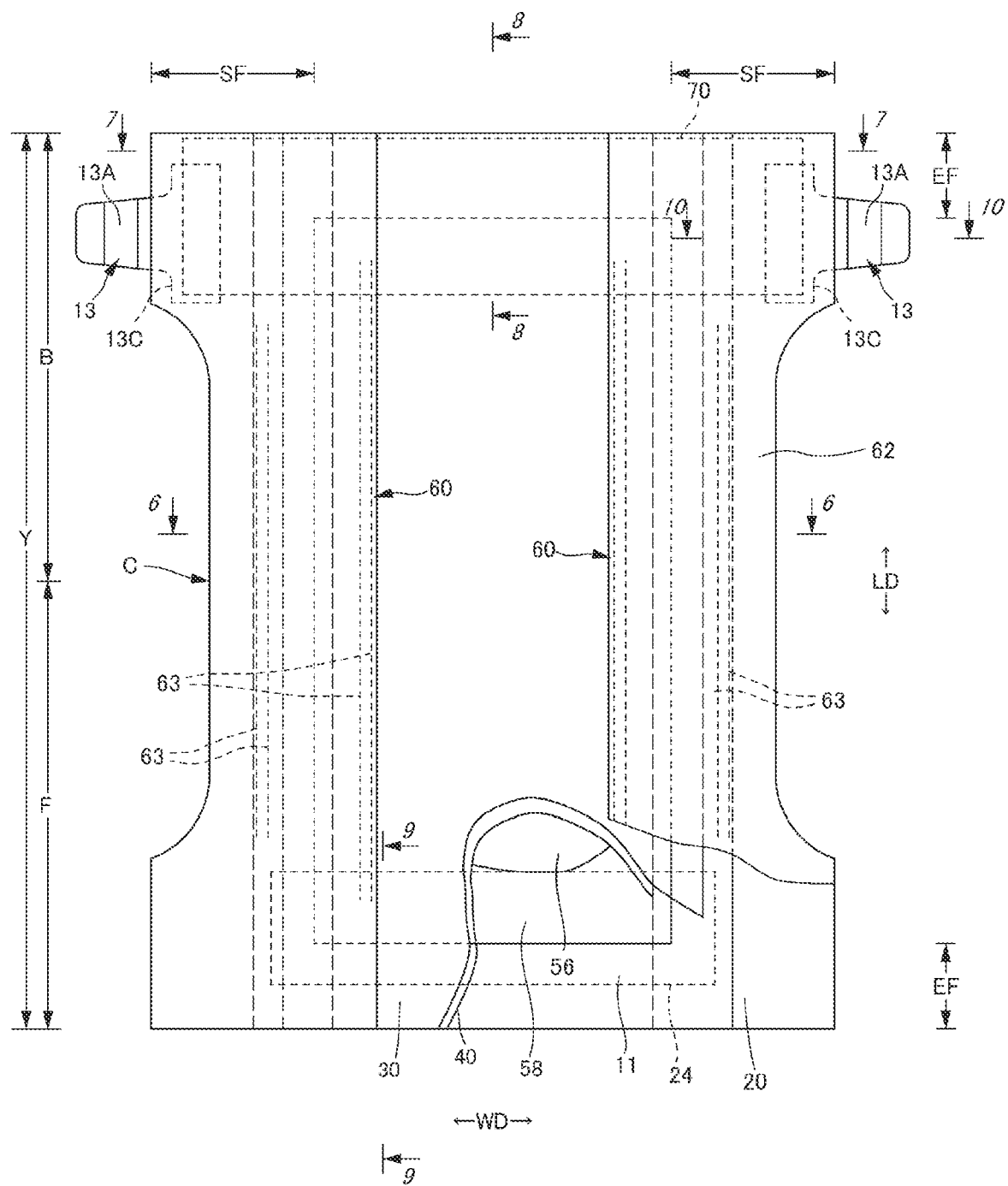
FIG. 16 is a plan view illustrating the inner surface of a tape-type disposable diaper in a spread state.

The outer members 12F and 12B are composed of the front outer member 12F which is a part constituting the front body F and the back outer member 12B which is a part constituting the back body B. The front outer member 12F and the back outer member 12B are not continuous on the crotch side but may be separated in the front-back direction LD (outer member separated type). The separation distance 12d can be set to, for example, about 150 to 250 mm. In addition, as illustrated in FIGS. 14 and 15, the outer member 12 may be an integral body that extends continuously from the front body F to the back body B through the crotch (outer member integrated type).

The outer members 12F and 12B have a waist portion which is a front-back direction range corresponding to the region T. In this embodiment, the front outer member 12F does not have a portion corresponding to the intermediate region L, but the back outer member 12B has a gluteal cover portion C extending from the lower torso region T to the intermediate region L side. Although not illustrated, the front outer member 12F is also provided with an inguinal cover portion extending from the lower torso region T to the intermediate region L side, or although the inguinal cover portion is provided, a gluteal cover portion is not provided. Further, it is not necessary to provide portions corresponding to the intermediate region L on both the front outer member 12F and the back outer member 12B. In the illustrated embodiment, the lower edge of the gluteal cover portion C is formed in a straight line along the width direction WD similarly to the lower edge of the front outer member 12F. However, the lower edge of the gluteal cover portion C may be a curve so as to be positioned on the waist opening side on the outside in the width direction.

As illustrated in FIGS. 4 and 5, the outer members 12F and 12B are formed by bonding an outer sheet layer 12S and an inner sheet layer 12H by a hot melt adhesive or a bonding means such as welding and the like. The sheet material forming the outer sheet layer 12S and the sheet material forming the inner sheet layer 12H may be a common sheet material as in the form illustrated in FIG. 5 or may be individual sheet materials. That is, in the former case, the inner sheet layer 12H and the outer sheet layer 12S are respectively formed by the inner portion and the outer portion of one sheet material folded back at the edge of the waist opening WO (which may be the crotch side edge). Incidentally, in the former embodiment, there is an advantage that the number of materials of the sheet material is small, and in the latter embodiment, there is an advantage that positional deviation is hard to occur when the inner sheet layer 12H and the outer sheet layer 12S are bonded together.

The sheet material used for the outer sheet layer 12S and the inner sheet layer 12H can be used without particular limitation, but a nonwoven fabric is preferable, and examples of the nonwoven fabric include synthetic fibers such as polyolefin type such as polyethylene and polypropylene, polyester type, polyamide type, and the like, mixed fibers in which two or more of these are used, and composite fibers. Further, the nonwoven fabric may be manufactured by any processing. Examples of the processing method include known methods such as a spun lace method, a spunbond method, a thermal bond method, a melt blown method, a needle punch method, an air-through method, and a point bond method. When a nonwoven fabric is used, its basis weight is preferably about 10 to 30 g/m$^2$.

Further, the total basis weight of the outer members 12F and 12B is preferably about 20 to 60 g/m$^2$.

(Stretchable Region/Non-stretchable Region)

The outer members 12F and 12B are provided with elongated elastic members 15 to 19 such as rubber thread or the like between the outer sheet layer 12S and the inner sheet layer 12H in order to enhance fitting to the wearer's waist, and a stretchable region which elastically expands and contracts in the width direction WD is formed accompanying expansion and contraction of the elastic member. In this stretchable region, the outer sheet layer 12S and the inner sheet layer 12H contract as the elastic member contracts in a natural length state, and wrinkles or pleats are formed. When the stretchable region elongates in the longitudinal direction of the elastic member, the outer sheet layer 12S and the inner sheet layer 12H can be elongated to a predetermined stretch rate at which the outer sheet layer 12S and the inner sheet layer 12H elongate without wrinkles. As the elongated elastic members 15 to 19, synthetic rubber may be used, and also natural rubber may be used.

For bonding the outer sheet layer 12S and the inner sheet layer 12H in the outer members 12F and 12B and fixing the elongated elastic members 15 to 19 sandwiched therebetween, at least one of hot melt adhesives to be applied by various application methods and a fixing means using material welding such as a heat sealing, ultrasonic sealing and the like can be used. It is preferable that the portions other than the adhesive portions of the elongated elastic members 15 to 19 are not adhered or weakly adhered since the flexibility deteriorates when the entire surfaces of the outer members 12F and 12B are tightly fixed. In the illustrated embodiment, by applying a hot melt adhesive only to the outer peripheral surfaces of the elongated elastic members 15 to 19 by an application means such as a comb gun or a sure wrap nozzle and sandwiching them between both sheet layers 12S and 12H, fixing of the elongated elastic members 15 to 19 to the both sheet layers 12S and 12H and fixing between the both sheet layers 12S and 12H are performed only by the hot melt adhesive applied to the outer peripheral surfaces of the elongated elastic members 15 to 19. The elastic members 15 to 19 can be fixed to the outer sheet layer 12S and the inner sheet layer 12H only at both ends in the extending direction in the stretchable region.

More specifically, between the outer sheet layer 12S and the inner sheet layer 12H in the waist portion W of the outer members 12F and 12B, a plurality of waist portion elastic members 17 is attached at intervals in the vertical direction so as to be continuously extend over entirely the width direction WD. One or a plurality of waist portion elastic members 17 disposed in a region adjacent to the lower waist portion U may overlap with the inner member 200 or may be provided on both sides in the width direction except for the central portion in the width direction overlapping with the inner member 200. As this elastic members 17 of the waist portion, about 3 to 22 rubber threads each having a fineness of 155 to 1880 dtex, particularly about 470 to 1240 dtex (in the case of synthetic rubber) (in the case of natural rubber, a cross-sectional area of about 0.05 to 1.5 mm$^2$, particularly about 0.1 to 1.0 mm$^2$) are preferably provided at an interval of 4 to 12 mm, such that a stretch rate of the width direction WD of the waist portion W is preferably about 150 to 400%, particularly about 220 to 320%. Further, it is not necessary to use the waist portion elastic member 17 having the same thickness or to set the same stretch rate in the entire front-back direction LD of the waist portion W. For example, at the upper portion and the lower portion of the waist portion W, the stretch rate of the waist portion elastic member 17 may be different.

In addition, between the outer sheet layer 12S and the inner sheet layer 12H in the lower waist portion U of the outer members 12F and 12B, a plurality of elastic members of the lower waist portions 15 and 19 composed of elongated elastic members are attached at intervals in the up-down direction.

As the elastic member of the lower waist portion portions 15 and 19, about 5 to 30 rubber threads each having a fineness of 155 to 1880 dtex, particularly about 470 to 1240 dtex (in the case of synthetic rubber) (in the case of natural rubber, a cross-sectional area of about 0.05 to 1.5 mm$^2$, particularly about 0.1 to 1.0 mm$^2$) are preferably provided at an interval of 1 to 15 mm, particularly 3 to 8 mm, such that a stretch rate of the width direction WD of the lower waist portion U is preferably about 200 to 350%, particularly about 240 to 300%.

Further, between the outer sheet layer 12S and the inner sheet layer 12H in the gluteal cover portion C of the back outer member 12B, a plurality of elastic members 16 of the cover portion composed of an elongated elastic member are attached at intervals in the up-down direction.

As the elastic member of the cover portion 16, about 2 to 10 rubber threads having a fineness of 155 to 1880 dtex, particularly about 470 to 1240 dtex (in the case of synthetic rubber) (in the case of natural rubber, a cross-sectional area of about 0.05 to 1.5 mm$^2$, particularly about 0.1 to 1.0 mm$^2$) are preferably provided at an interval of 5 to 40 mm, particularly 5 to 20 mm, such that a stretch rate of the width direction WD of the cover portion is preferably about 150 to 300%, particularly about 180 to 260%.

Similarly, in the case where an inguinal cover portion is provided on the front outer member 12F, it is possible to provide the elastic member of the cover portion.

When the elastic members 15, 16, and 19 are provided in the front-back direction range having the absorber 56 like the lower waist portion U and the gluteal cover portion C in the illustrated embodiment, to prevent contraction of the absorber 56 in the width direction WD in part or the whole of the range, the intermediate portion in the width direction (preferably including the entire inner and outer joined portion 201) including a part or the whole of the portion overlapping with the absorber 56 in the width direction WD is a non-stretchable region A1, and both sides in the width direction is a stretchable region A2. It is preferable that the waist portion W is formed as the stretchable region A2 over the entire width direction WD. However, similarly to the lower waist portion U, the non-stretchable region A1 may be provided in the middle in the width direction.

The stretchable region A2 and the non-stretchable region A1 can be constructing by supplying the elastic members 15 to 17 and 19 between the inner sheet layer 12H and the outer sheet layer 12S, fixing the elastic members 15, 16, and 19 in the stretchable region A2 at least at the both ends in the extending direction via a hot melt adhesive, not fixing in the region to be the non-stretchable region A1, in the region to be the non-stretchable region A1, cutting the elastic members 15, 16, and 19 by pressing and heating at one place in the middle of the width direction, or finely cutting almost all of the elastic members 15, 16, 19 by pressing and heating, such that the elasticity is remained in the stretchable region A2 while killing the elasticity in the non-stretchable region A1. In the former case, as illustrated in FIG. 4, in the non-stretchable region A1, a cutting remainder continuing from the elastic members 15, 16, and 19 of the stretchable region A2 is remained between the outer sheet layer 12S and the inner sheet layer 12H in a state individually contracting to a natural length as an idle elastic member 18. In the latter case, although not illustrated, the cutting remainder continuing from the elastic members 15, 16, 19 of the stretchable region A2 and cut pieces of the elastic members not continuous with the elastic members 15, 16, and 19 of the stretchable region A2 are remained between the outer sheet layer 12S and the inner sheet layer 12H in a state of individually contracting to a natural length as an ideal elastic member.

In outer member separated type underpants type disposable diapers, since the inner member 200 is exposed between the front outer member 12F and the back outer member 12B, in order to prevent the liquid impervious sheet 11 from being exposed on the back surface of the inner member 200, the cover nonwoven fabric 20 that covers the back surface of the inner member 200 from a space between the front outer member 12F and the inner member 200 to a space between the back outer member 12B and the inner member 200 is provided. In the embodiment illustrated in FIGS. 14 and 15, in the case where the outer sheet layer 12S of the outer member 12 is a nonwoven fabric, the outer sheet layer 12S is continuous from the front body F to the back body B through the crotch to be the cover nonwoven fabric 20 covering the liquid impervious sheet 11 of the inner member 200.

Figure 8:
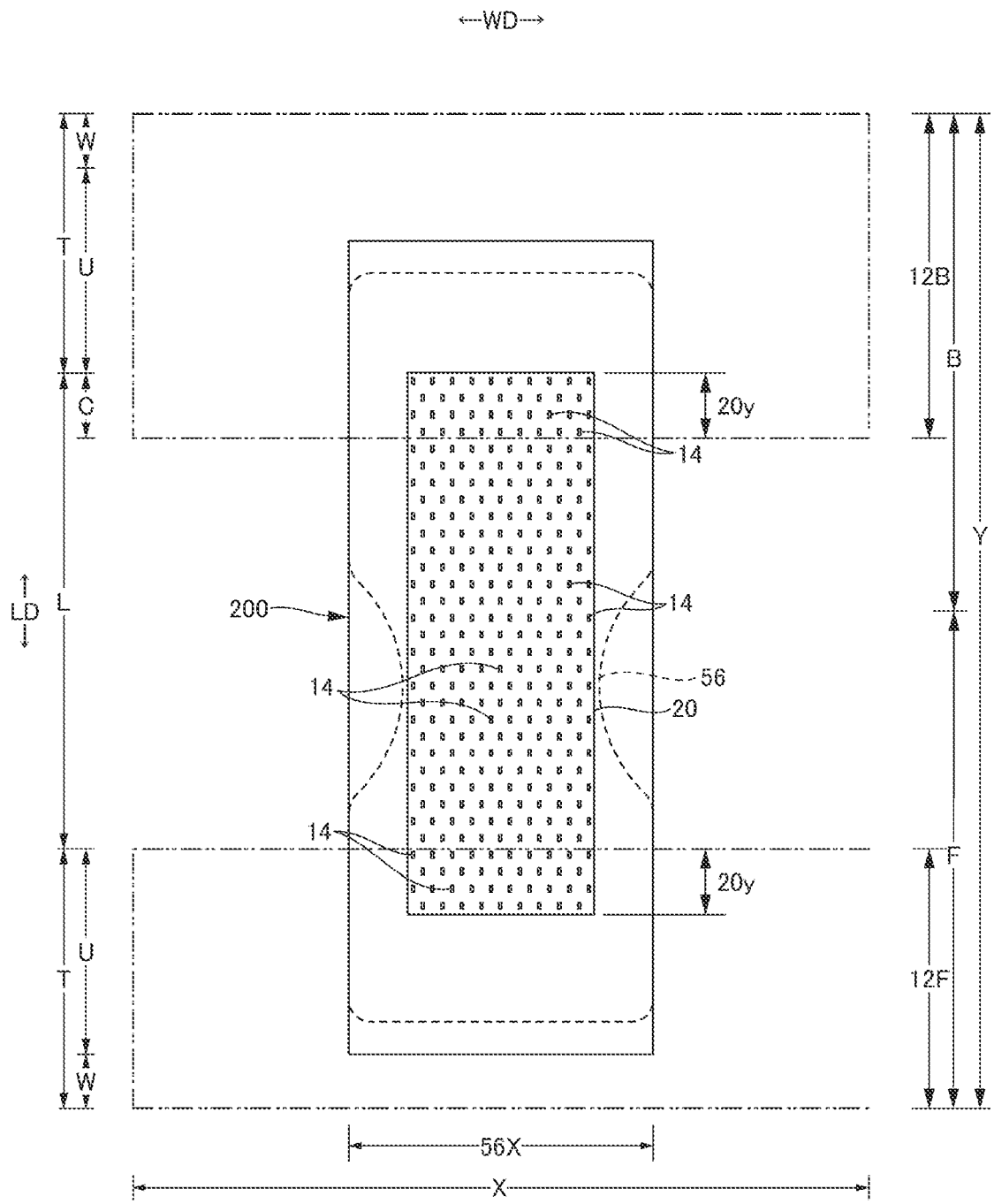
FIG. 8 is a plan view illustrating the outer surface of the inner member in a spread state together with the outline of an outer member.
Figure 9:
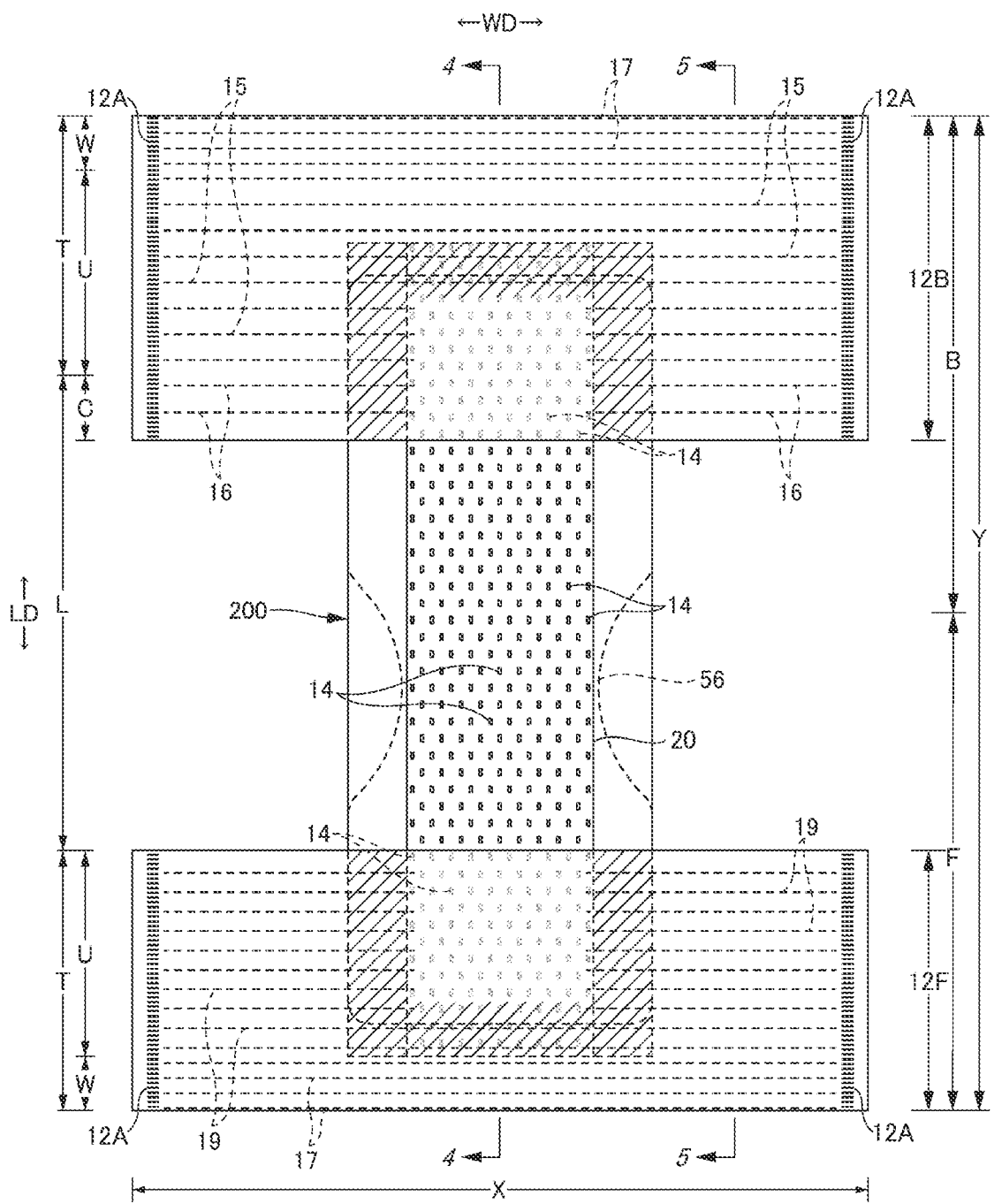
FIG. 9 is a plan view illustrating the outer surface of an underpants-type disposable diaper in a spread state.
Figure 10:
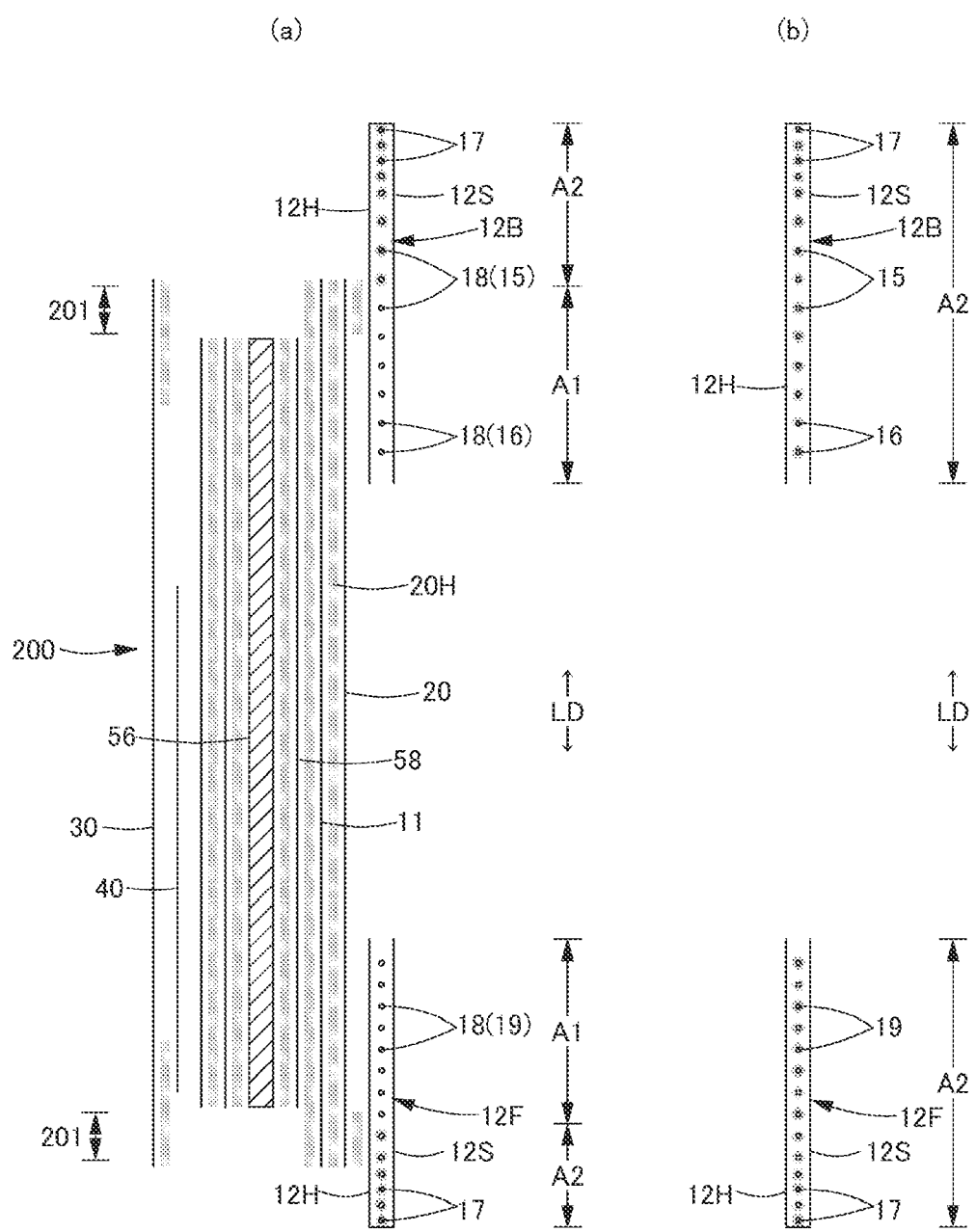
FIG. 10(a) is a cross-sectional view taken along line 4-4 in FIG. 9.
FIG. 10(b) is a cross-sectional view taken along line 5-5 in FIG. 9.

The range of the cover nonwoven fabric 20 in the front-back direction is not particularly limited as long as it has a portion overlapping with the front outer member 12F and the back outer member 12B. As illustrated in FIGS. 2, 5, 7, 9, and 10, the range may extend in the front-back direction LD over entirely from the front end to the back end of the inner member 200, or as illustrated in FIG. 8, the range may extend in the front-back direction LD from the intermediate position in the front-back direction of the region where the front outer member 12F and the inner member 200 overlap to the intermediate position in the front-back direction of the region where the back outer member 12B and the inner member 200 overlap. In the latter case, a length 20y in the front-back direction of the overlapping portion of the cover nonwoven fabric 20 and the front outer member 12F and a length 20y in the front-back direction of the overlapping portion of the cover nonwoven fabric 20 and the back outer member 12B can be appropriately determined, in the usual case, the length y can be set to about 20 to 40 mm each.

A range in the width direction of the cover nonwoven fabric 20 is a range within which the back side exposed portion of the liquid impervious sheet 11 can be concealed. Therefore, in the illustrated embodiment, since the liquid impervious sheet 11 is exposed between the base of the right and left side gathers 60, the cover nonwoven fabric 20 is provided so as to cover a range in the width direction from a back surface side of the base portion of at least one of the side gathers 60 to the back surface side of the base portion of the other side gather 60. As a result, it is possible to conceal the liquid impervious sheet 11 with the cover nonwoven fabric 20 and the gather nonwoven fabric 62 of the side gathers 60, and the holes 14 at both ends of the cover nonwoven fabric 20 in the width direction are not concealed by the gather nonwoven fabric 62 when viewed from the outer surface. In addition, even if both end portions in the width direction of the cover nonwoven fabric 20 do not cover the back surface side of the base portion of the side gather 60, and the gather nonwoven fabric 62 covers the back surface side of the both ends of the cover nonwoven fabric 20 in the width direction, it is possible to conceal the liquid impervious sheet 11 with the cover nonwoven fabric 20 and the gather nonwoven fabric 62. In that case, if the total luminous transmittance of the gather nonwoven fabric 62 is 60 to 90%, the hole 14 of the perforated nonwoven fabric can be sufficiently visually confirmed through the portion where the gather nonwoven fabric 62 conceals the cover nonwoven fabric 20. Therefore, it can be recognized that the portion having the air-permeability-improving function extends to the side gathers 60, and the visual effect of the hole 14 is sufficiently exerted.

<Example of Tape-Type Disposable Diaper>

FIGS. 16 to 20 illustrate examples of a tape-type disposable diaper, in which the reference sign X indicates the maximum width of the diaper excluding a fastening tape, and the reference sign Y indicates the entire length of the diaper. This tape-type disposable diaper has the absorber 56 extending from the ventral side to the dorsal side, a liquid pervious top sheet 30 covering the front surface side of the absorber 56, and a liquid impervious sheet 11 covering the back surface side of the absorber 56. The tape-type disposable diaper includes a ventral side end flap portion EF, a dorsal side end flap portion EF, and a pair of side flap portions SF. The ventral side end flap portion EF and the dorsal side end flap portion EF are portions extending to the front side and the back side of the absorber 56 respectively and not including the absorber 56, and a pair of the side flap portions SF extends laterally from the side edge of the absorber 56. A constriction along the leg portion is formed in the middle in the front-back direction of the side flap portion SF, and a fastening tape 13 is provided on the dorsal side of the constricted portion.

The back surface of the liquid impervious sheet 11 is covered with the cover nonwoven fabric 20. The cover nonwoven fabric 20 extends to the peripheral edge of a diaper, the liquid impervious sheet 11 extends to the front and back edges of the diaper in the front-back direction and extends in the width direction between the side edge of the absorber and the side edge of the cover nonwoven fabric 20. However, the cover nonwoven fabric 20 can be formed only partially in the front-back direction, only partially in the width direction, or both, if necessary. For example, when a part of the liquid impervious sheet 11 is covered with another material such as a gather nonwoven fabric or the like, the cover nonwoven fabric 20 may not be provided for that part.

In the illustrated example, the top sheet 30 and the liquid impervious sheet 11 are rectangular in shape and have somewhat larger sizes in the front-back direction and the width direction than the absorbent element 50. The peripheral edges protruding from the side edges of the absorbent element 50 in the top sheet 30 and the peripheral edges protruding from the side edge of the absorbent element 50 in the liquid impervious sheet 11 are joined by a hot melt adhesive or the like.

Further, as with the underpants-type disposable diaper, the absorber 56 can be interposed between the top sheet and the liquid impervious sheet as an absorbent element wrapped by a packaging sheet, and the intermediate sheet 40 can be provided between the top sheet and the absorbent element. The intermediate sheet 40 in the illustrated embodiment is disposed at the center shorter than the width of the absorbent element 50, but may be provided over the entire width. The length of the intermediate sheet 40 in the longitudinal direction may be the same as the maximum length of a diaper, may be the same as the length of the absorbent element 50, or may be within a short length range around a region receiving a liquid. Furthermore, as with the underpants-type disposable diaper, it is also possible to provide a indicator which discolors when it contacts with the liquid content of excrement.

On both sides in the width direction of the surface of a tape-type disposable diaper, the side gathers 60 are respectively provided. Each side gather 60 has a first portion 61 (planner gather portion) provided in each side flap portion SF and a second portion 69 (three-dimensional gather) projecting on both sides of the top sheet 30. More specifically, the belt shaped gather nonwoven fabric 62 having a length equal to the maximum length of a diaper Y extends from the first portion 61 to the second portion 69, in the first portion 61, the gather nonwoven fabric 62 is bonded to the cover nonwoven fabric 20 with a hot melt adhesive or the like, and between these nonwoven fabrics, one gather elastic member 63 along the front-back direction LD is fixed in a stretched state, or a plurality of the gather elastic members 63 is fixed at intervals in the width direction WD in a stretched state. Due to the contraction force, the first portion 61 contracts in the front-back direction LD to be a planar gather in contact with the leg portion. Further, the gather nonwoven fabric 62 has an extending portion extending from the first portion 61 as the root portion to the center side in the width direction WD. At least this extending portion is folded at the tip to have a two-layer structure. Both end portions in the front-back direction LD of the extending portion are made to be the fallen portion 67 fixed to the top sheet 30. On the other hand, the intermediate portion in the front-back direction LD positioned therebetween is a non-fixed free portion 68. In the free portion 68, one gather elastic member 63 along the front-back direction LD is fixed in a stretched state in a stretched state, or a plurality of the gather elastic members 63 is fixed in a stretched state at intervals in the width direction WD, and the free portion 68 of the second portion 69 contracts in the front-back direction LD due to its contraction force and becomes a three-dimensional gather in contact with a leg portion.

The fastening tape 13 in the illustrated embodiment includes a sheet base material forming a tape attaching portion 13C fixed to the side portion of the diaper and a tape main unit section 13B projecting from the tape attaching portion 13C, and an engagement portion 13A with respect to the ventral side, which is provided at the intermediate portion in the width direction of the tape main unit section 13B in the seat base material. A tip end side of the engagement portion 13A is a tab portion. The tape attaching portion 13C of the fastening tape 13 is sandwiched between the gather nonwoven fabric 62 forming the inner layer in the side flap portion and the cover nonwoven fabric 20 forming the outer layer and is adhered to both the sheets 62 and 12 with the hot melt adhesive. The engagement portion 13A is bonded to the inner surface of the tape main unit section 13B by an adhesive.

A hook member (male member) of a mechanical fastener (hook and loop fastener) is suitable as the engagement portion 13A. The hook member has a large number of engagement projections on its outer surface side. The engagement projection has (A) a check mark shape, (B) a J shape, (C) a mushroom shape, (D) a T shape, and (E) a double J shape (a shape bonded back to back of a J shape), but may have any shape. Obviously, an adhesive material layer can also be provided as an engagement portion of the fastening tape 13.

As the sheet base material forming from the tape attaching portion 13C to the tape main unit section 13B, a nonwoven fabric, a plastic film, a polyethylene laminated nonwoven fabric, paper, or a composite material thereof can be used.

Upon wearing the diaper, the fastening tape 13 is engaged in place on the ventral side outer surface with the side flap portion SF on the dorsal side superimposed on the outside of the side flap portion SF on the ventral side. The position and the size of the fastening portion of the fastening tape 13 can be arbitrarily determined.

It is preferable to provide a target sheet 24 having a target for facilitating engagement at the engagement portion of the fastening tape 13 on the ventral side. In the case where the engagement portion 13A is a hook member, as the target sheet 24, a film type having a film layer and an engaging layer to be detachably engaged with a hook of the engagement portion 13A provided on the entire outer surface thereof can be suitably used. As the engaging layer in this case, besides a form in which a mesh woven mesh body having a loop is attached on the film layer, a form in which a nonwoven fabric layer of a thermoplastic resin is mounted on the film layer by intermittent ultrasonic sealing, and fibers of a nonwoven fabric form a loop is known, but any of them can be suitably used. Further, a filmless type target tape which is obtained by embossing a nonwoven fabric of thermoplastic resin and has no film layer can be used. In these target tapes, the hook of the fastening tape 13 is entangled or caught in the loop, whereby the fastening tape 13 is bonded.

In the case where the engagement portion 13A is an adhesive layer, it is possible to use a sheet base material made of a plastic film having a smooth surface, which is rich in adhesiveness, and subjected to a peeling process.

In the case where the engagement point of the fastening tape 13 in the ventral side is made of a nonwoven fabric, for example, when the cover nonwoven fabric 20 in the illustrated embodiment is made of a nonwoven fabric, and the engagement portion 13A of the fastening tape 13 is a hook member, the target sheet 24 may be omitted, and the hook member can be entangled and engaged with the nonwoven fabric of the cover nonwoven fabric 20. In this case, the target sheet 24 may be provided between the cover nonwoven fabric 20 and the liquid impervious sheet 11.

The end flap portion EF is a portion extending to the front side and the back side of the absorbent main unit section 10 respectively and not having the absorbent element 50. The front extended portion is the ventral side end flap portion EF, and the back extended portion is the dorsal side end flap portion EF.

The length in the front-back direction of the dorsal side end flap EF is preferably the same as or shorter than the length in the front-back direction of the attachment portion of the fastening tape 13 for the reasons described above. Further, when the dorsal side end portion and the absorbent element 50 are too close, a gap tends to be formed between the diaper dorsal side end portion and the body surface due to the thickness and elasticity of the absorbent element 50, and therefore the length is preferable to set it to 10 mm or more.

The front-back direction length of the end flap portion EF on the ventral side and the end flap portion EF on the dorsal side is preferably about 5 to 20% of the length L in the front-back direction of the entire diaper, and in the diaper for infants, 10 to 60 mm, especially 20 to 50 mm, is suitable.

In order to improve the fitting on the dorsal side of a diaper, it is preferable that a belt shaped dorsal side stretchable sheet 70 elastically stretchable in the width direction is provided between both fastening tapes 13 as in the illustrated embodiment. It is preferable that both ends of the dorsal side stretchable sheet 70 extend to a site overlapping with the attachment portion of both fastening tapes 13, but it may be separated to the center side in the width direction. It is preferable that the dorsal side stretchable sheet 70 has a dimension in the front-back direction within a range of about plus or minus 20% with respect to the dimension in the front-back direction of the attachment portion of the fastening tape 13. As illustrated in the drawing, when the dorsal side stretchable sheet 70 is disposed so as to overlap with the boundary line between the dorsal side end flap portion EF and the absorbent element 50, it is preferable because the dorsal side end portion of the absorbent element 50 is firmly pressed against the body. As the dorsal side stretchable sheet 70, a sheet-like elastic member such as a rubber sheet may be used, but from the viewpoint of air permeability, it is preferable to use a nonwoven fabric or paper. In this case, although it is possible to use an air-permeable sheet-like elastic member such as an elastic nonwoven fabric, as illustrated in FIG. 20(*a*), a structure in which a sheet base material 71 such as two nonwoven fabrics or the like is bonded with an adhesive such as a hot melt adhesive, and an elastic member 72 such as a sheet-like, mesh-like, elongated (thread-like or string-like) or the like that is perforated is fixed in a stretched state in the width direction between the two sheet base materials 71, is preferably used. The stretch rate of the elastic member 72 is preferably about 150 to 250%. In the case of using the elastic member 72 in the form of an elongated shape (thread-like or string-like), it is preferable to provide about five to fifteen members each having a thickness of 420 to 1120 dtex at intervals 72*d* of 3 to 10 mm.

In addition, as illustrated, when a part of the elastic member 72 is disposed so as to traverse the absorbent element 50, the fitting of the absorbent element 50 is improved, which is preferable. In this case, if a part or the whole of the portion where the elastic member 72 overlaps with the absorbent element 50 is made such that a contraction force does not act by a means such as cutting, fitting is further improved since the dorsal side end portion of the absorbent element 50 does not shrink in the width direction.

The elastic member 72 may be fixed over the maximum length of the sheet base material 71 in the longitudinal direction of the sheet (width direction of a diaper), but to prevent shrinkage and turn-up at the time of attachment to the diaper main unit, it is preferable that no contraction force acts, or the elastic member 72 is not provided in the range of about 5 to 20 mm at the end portion in the front-back direction (width direction of the diaper) of the sheet.

In the illustrated embodiment, although the dorsal side stretchable sheet 70 is sandwiched between the gather nonwoven fabric 62 and the cover nonwoven fabric 20 on both sides in the width direction of the liquid impervious sheet 11 and is provided so as to be sandwiched between the liquid impervious sheet 11 and the absorbent element 50 in a site overlapping with the liquid impervious sheet 11, the dorsal side stretchable sheet 70 may be provided between the liquid impervious sheet 11 and the cover nonwoven fabric 20 or may be provided on the outer surface of the cover nonwoven fabric 20 or between the top sheet 30 and the absorbent element 50. The dorsal side stretchable sheet 70 may be provided on the top sheet 30. In this case, it may be provided on the gather nonwoven fabric 62 on both sides in the width direction of the liquid impervious sheet 11. Further, in the case where the cover nonwoven fabric 20 is formed by stacking a plurality of sheet base materials, the entire dorsal side stretchable sheet 70 may be provided between the sheet base materials of the cover nonwoven fabric 20.

<Cover Nonwoven Fabric>

The cover nonwoven fabric 20 covers the back surface side of the liquid impervious sheet 11 and forms the outer surface of the product in at least a part of the portion covering the liquid impervious sheet 11. Characteristically, the cover nonwoven fabric 20 is a perforated nonwoven fabric in which a large number of holes 14 penetrating the front and back are provided at intervals. The type of fiber of the cover nonwoven fabric 20 and the method of processing fiber binding (entanglement) are not particularly limited, but it is preferable to use an air-through nonwoven fabric, in which case it is preferable that the basis weight is 20 to 30 g/m$^2$, and the thickness is 0.3 to 1.0 mm.

Further, in the above-described outer member separated type underpants-type disposable diaper, if the side edge of the cover nonwoven fabric 20 is positioned on the same side as the side edge of the narrowest portion (the maximum width in the case of not having the constricted portion 56N. The narrowest portion in the constricted portion 56N in the case of having the constricted portion 56N) of the absorber 56 or on the center side in the width direction, the cover nonwoven fabric 20 is positioned only at the portion where the entire cover nonwoven fabric 20 overlaps with the absorber 56, that is, the portion where the rigidity is high, and wrinkles and folds are unlikely to occur. Therefore, it is difficult for both sides of the cover nonwoven fabric 20 to shrink in the front-back direction LD, and wrinkles are formed on both sides of the cover nonwoven fabric 20, or crushing of the hole 14 is difficult to occur.

In consideration of the effect of improving the air permeability, it is desirable that the cover nonwoven fabric 20 has the holes 14 throughout the front-back direction, but may have a region without the holes 14 in a part of the front-back direction LD. On the other hand, in the width direction WD, it is preferable that the hole 14 is provided throughout the cover nonwoven fabric 20. That is, in the embodiment in which both ends of the cover nonwoven fabric 20 in the width direction WD have regions without the holes 14, if the hole 14 is opened by a method other than punching with a cutter, as will be described later, the fibers at the edge portion of the hole 14 are retracted outside or in the vertical direction, the edge portion of the hole 14 warps, and the thickness of the perforated region is thicker than that of the nonporous region. Therefore, when storing the material of the cover nonwoven fabric 20 in a rolled state, the part of the nonporous region is loosely wound, and wrinkles and folds may be formed in the nonporous region on both sides. Therefore, it is desirable that the hole 14 be formed throughout the width direction WD like the illustrated embodiment.

Figure 2:
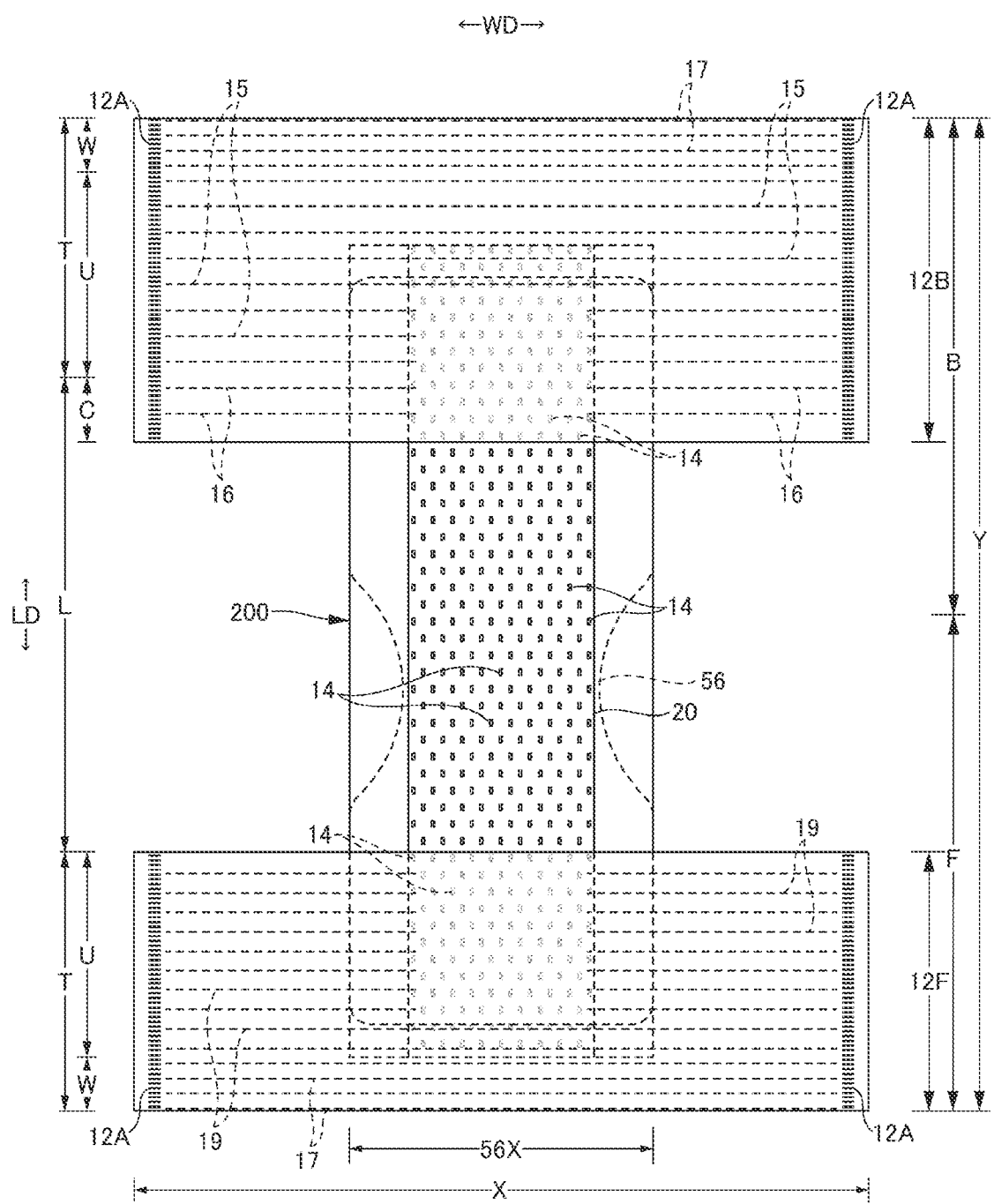
FIG. 2 is a plan view illustrating the outer surface of an underpants-type disposable diaper in a spread state.
Figure 17:
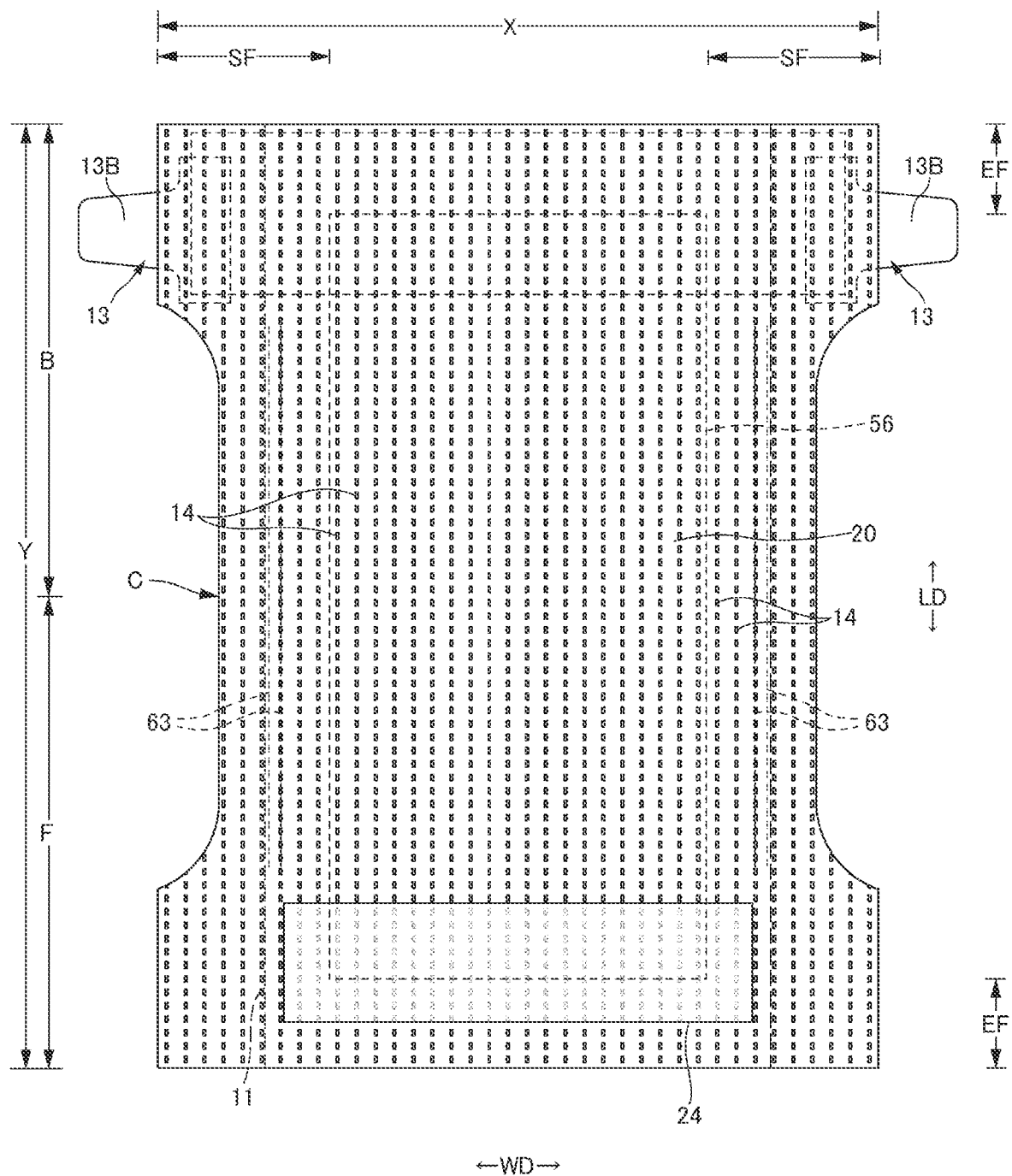
FIG. 17 is a plan view illustrating the outer surface of a tape-type disposable diaper in a spread state.
Figure 18:
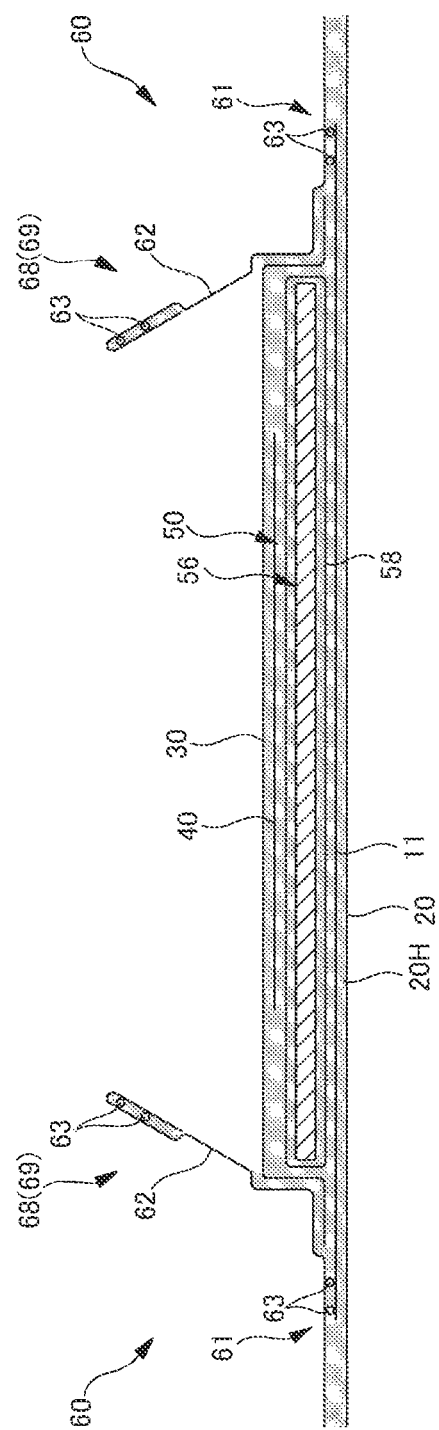
FIG. 18 is a cross-sectional view taken along line 6-6 in FIG. 16.
Figure 19:
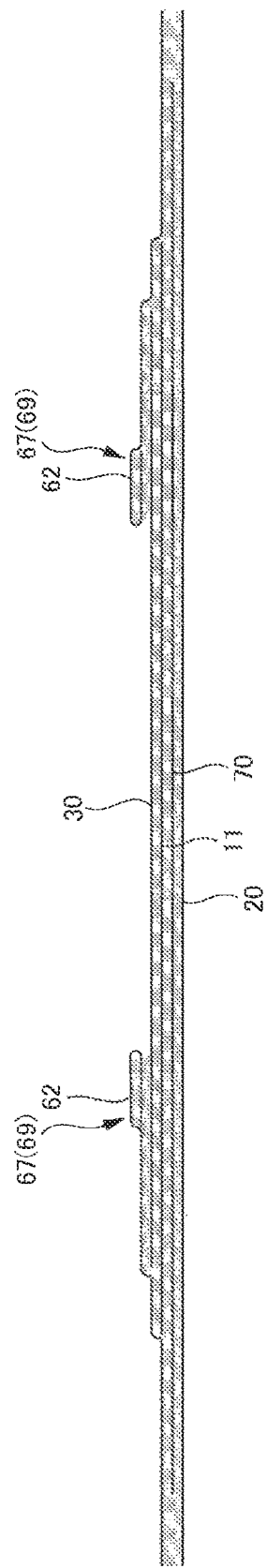
FIG. 19 is a cross-sectional view taken along line 7-7 in FIG. 16.

For example, in the above-described outer member-integrated type underpants type disposable diaper, as illustrated in FIG. 14, it is possible to form the hole 14 only in the intermediate region in the front-back direction which does not have the elastic members 15 to 18 in the cover nonwoven fabric 20. On the other hand, in the above-described tape type disposable diaper, as illustrated in FIG. 17, it is possible to form the hole 14 throughout the front-back direction and the width direction of the cover nonwoven fabric 20. Further, in the above-described outer member separated type underpants-type disposable diaper, as illustrated in FIGS. 2 and 8, it is desirable that the formation region of the hole 14 extends from a portion of the cover nonwoven fabric 20 overlapping with the front outer member 12F to a portion overlapping with the back outer member 12B.

Figure 21:
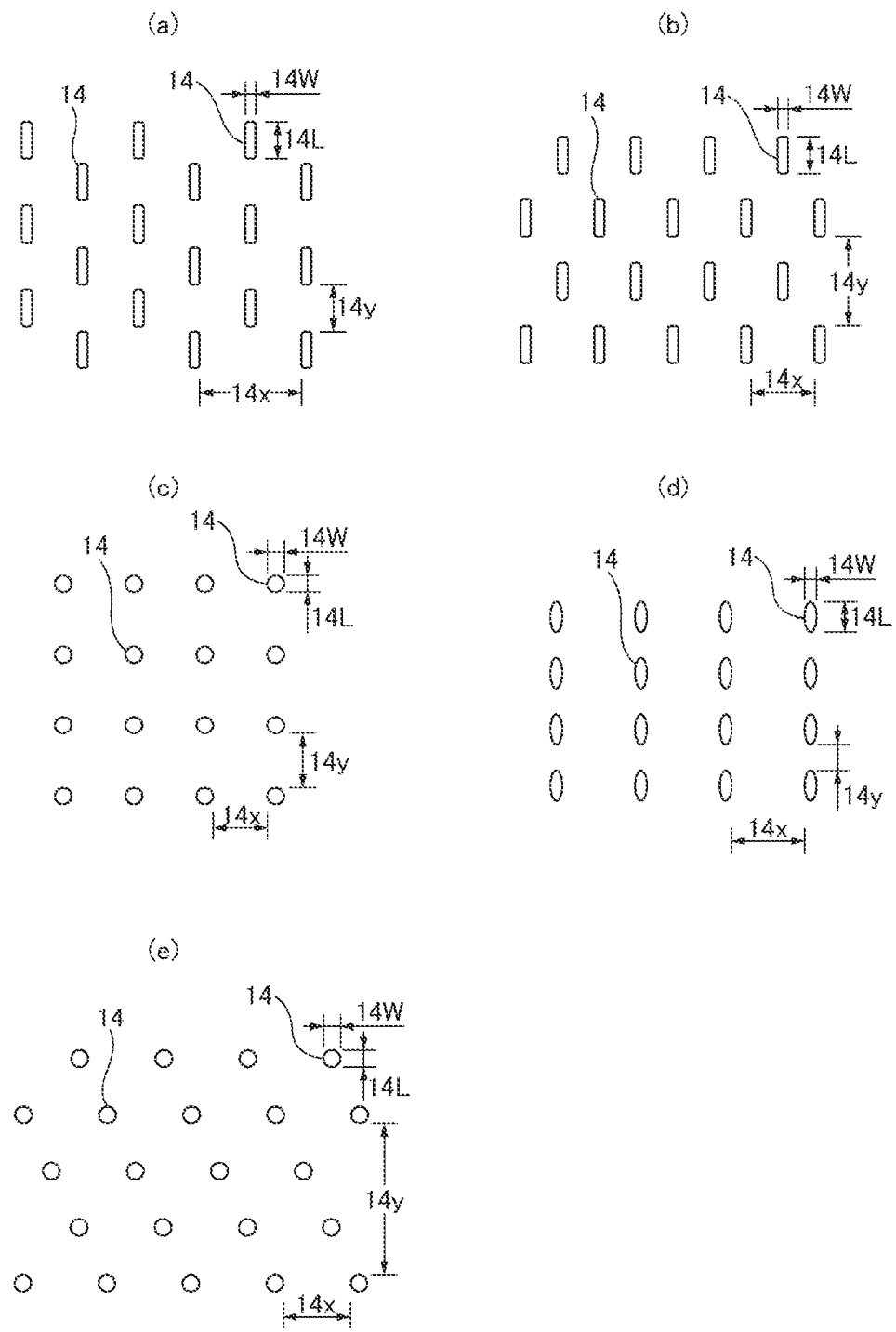
FIG. 21 is an enlarged plan view of a main part of a cover nonwoven fabric.

The planar shape (opening shape) of each hole 14 can be appropriately determined and may be an elongated hole shape as illustrated in FIGS. 21(a) and 21(b) and also may be an arbitrary shape such as a circular shape as illustrated in FIGS. 21(c) and 21(e), a polygon such as an ellipse, a triangle, a rectangle, a rhombus, or the like as illustrated in FIGS. 21(d), a star shape, a cloud shape, or the like. The dimension of each hole 14 is not particularly limited, but it is preferable that the maximum dimension 14L in the front-back direction LD is preferably 0.3 to 1.8 mm, particularly 0.4 to 1.0 mm, and the maximum dimension 14W in the width direction WD is 0.2 to 1.5 mm, particularly 0.3 to 1.0 mm. When the shape of the hole 14 is a long shape in one direction (the maximum length in one direction is longer than the maximum length in a direction orthogonal thereto) such as a long hole shape, an elliptic shape, a rectangular shape, a rhombic shape, or the like, it is preferable that the maximum in the longitudinal direction is 1.2 to 2.5 times the maximum dimension in the direction orthogonal thereto. When the shape of the hole 14 is long in one direction, it is desirable that the longitudinal direction of the hole 14 is the front-back direction LD, but it may be the width direction WD or the oblique direction.

The area and the area ratio of each hole 14 may be appropriately determined, but the area is preferably about 0.1 to 2.7 mm$^2$ (especially about 0.1 to 1.0 mm$^2$), the area ratio is 1.0 to 15.0% (particularly 5.0 to 10.0%).

Although the planar arrangement of the hole 14 can be appropriately determined, a regularly repeated plane arrangement is preferred. In addition to the regularly repeated plane arrangement such as an oblique lattice shape as illustrated in FIG. 21(a), a hexagonal lattice shape (also referred to as a zigzag shape) as illustrated in FIG. 21(b), a square lattice shape as illustrated in FIG. 21(c), a rectangular lattice shape as illustrated in FIG. 21(d), and a parallel lattice shape as illustrated in FIG. 21(e) (two groups of many parallel oblique direction rows are provided so as to cross each other) (including those inclined at an angle of less than 90° with respect to the front-back direction LD), a group of the hole 14 (the group may be regularly or irregularly arranged, and may be a pattern or a letter shape) can be regularly repeated.

The front-back direction interval 14y and the width direction interval 14x of the holes 14 can be appropriately determined, but considering air permeability, it is desirable that 14y be in the range of 0.9 to 8.0 mm, and 14x be in the range of 2.0 to 10 mm, in particular, 14y be in the range of 1.0 to 3.0 mm, and 14x be in the range of 3.0 to 5.0 mm. In particular, as illustrated in FIG. 21(d), if a row of the holes 14 aligned in the front-back direction at the front-back direction interval 14y narrower than the maximum dimension 14L of the hole 14 in the front-back direction is repeated at a predetermined interval in the width direction WD, and the width direction interval 14x is wider than the dimension 14L of the hole 14 in the front-back direction (it is more preferable if the width direction interval 14x is three times or more wider than the width direction dimension 14W of the hole 14), improvement in air permeability is remarkable, while softness and bulkiness are not impaired. In addition, it is preferable because there is no decrease in the tensile strength of a sheet in the front-back direction which is important in manufacturing. In particular, in this case, it is preferable that the shape of the hole 14 is elongated in the front-back direction LD.

As illustrated in FIG. 11, the peripheral portion of the hole 14 is a warped portion 14e warping to the front surface side. Specific examples of the shape includes the first embodiment and the second embodiment. In the first embodiment, the warped height 14h of the warped portion 14e is substantially uniform as illustrated in FIG. 22, and in the second embodiment, the warped portion 14e has a facing portion having the highest warping height 14i and a facing portion facing in a direction orthogonal thereto and having the lowest warping height 14j as illustrated in FIG. 23. It is desirable that the warped portion 14e be continuously formed in a cylindrical shape in the circumferential direction of the hole, but the warped portion 14e of a part or all of the holes 14 may be formed only in a part of the hole 14 in the circumferential direction. The warped heights 14h, 14i, and 14j (apparent height under no pressure measured with an optical microscope) are preferably about 0.2 to 1.2 mm, and in the second embodiment, the highest warping height 14i is preferably about 1.1 to 1.4 times the lowest warping height 14j. As can be seen from the second embodiment, the warping height may change in the circumferential direction of the hole 14.

The hole 14 may be a punched hole 14 whose peripheral edge is formed by a cut ends of the fibers and may be a non-punched hole 14 (the fiber density of an edge portion is high) having few cut ends of the fibers at the peripheral edge of the hole 14 and being formed by pushing and inserting a pin between the fibers. For example, if the hole 14 having a long shape in one direction is formed by inserting a pin, the fibers around the hole 14 are retracted outside or in a vertical direction to form the warped portion (burr) 14e, and the warping height i of the facing portion of the hole 14 in the longitudinal direction is higher than the warping height j of the facing portion in the direction orthogonal to the longitudinal direction. Peripheral portions of the holes 14 may be lower in fiber density than the surrounding portions, but preferably equal or higher. Further, it is desirable that the fibers at the edge of the hole 14 are fused to each other, but they may not be fused.

The cover nonwoven fabric 20 is fixed to the liquid impervious sheet 11 (corresponding to the support sheet of the present invention) via a hot melt adhesive 20H. The fixing region of the cover nonwoven fabric 20 is defined as the entire front-back direction and the entire width direction of the cover nonwoven fabric 20, or a part thereof may be non-fixed. For example, in the above-described outer member separated type underpants type disposable diaper, if both ends in the width direction of the cover nonwoven fabric 20 are not fixed, even if the side portion of the absorber 56 is somewhat contracted due to the influence of the side gathers 60, it is less likely to be affected thereby, and there is an advantage that wrinkles and folds are hardly formed on the cover nonwoven fabric 20. In this case, the width of the non-fixed portion at both ends in the width direction of the cover nonwoven fabric 20 may be suitably determined, but it may be, for example, 3 to 10 mm, preferably 5 to 8 mm.

Characteristically, as illustrated in FIG. 11, at least the tip portion of the warped portion 14e of the cover nonwoven fabric 20 is an adhesive portion bonded to the liquid impervious sheet 11 via the hot melt adhesive 20H, and portions other than this adhesive portion are non-adhered. With such a bonded structure, since the adhering area is reduced, the flexibility is not impaired and the peripheral portion of the hole 14 can be securely fixed to the liquid impervious sheet 11. In particular, since the warped portion 14e supports the cover nonwoven fabric 20 with respect to the liquid impervious sheet 11 like a prop, the warped portion 14e becomes bulky and has excellent air permeability as compared with a nonporous nonwoven fabric having the same basis weight.

Examples of a representative adhering state includes, as illustrated in FIG. 11(a), a state where only the tip portion of the warped portion 14e is adhered to the liquid impervious sheet 11 via the hot melt adhesive 20H, as illustrated in FIG. 11(b), a state where the whole of the warped portion 14e is adhered to the liquid impervious sheet 11 via the hot melt adhesive 20H, as illustrated in FIG. 11(c), a state where the entire outer side of the warped portion 14e from the inner portion of the tip portion is adhered to the liquid impervious sheet 11 via the hot melt adhesive 20H, and the inner portion of the tip portion is not adhered. Although it is desirable that no adhesive exists on the inner peripheral surface of the hole 14 of the warped portion 14e and the site of the liquid impervious sheet 11 overlapping with the hole 14, it may be somewhat protruded.

The adhering state of the warped portion 14e is not limited to the illustrated embodiment form as long as at least the tip portion is attached to the liquid impervious sheet 11 via the hot melt adhesive 20H, and at least a part of the circumferential direction of the hole 14 may be in any one of the above adhering states. For example, as illustrated in FIGS. 22 and 23, in the case where the warped portion 14e is continuous in the circumferential direction of the hole 14, it is preferable that the entire circumferential direction of the barrel shaped tip portion is in the above adhering state, but a part thereof may be in another adhesion state or non-adhesive. In addition, in the case where the warped portion 14e is formed only in a part of the hole 14 in the circumferential direction, it suffices that the tip portion of the portion is in the above adhering state. Further, different adhering states may be mixed in many of the warped portions 14e.

Figure 24:
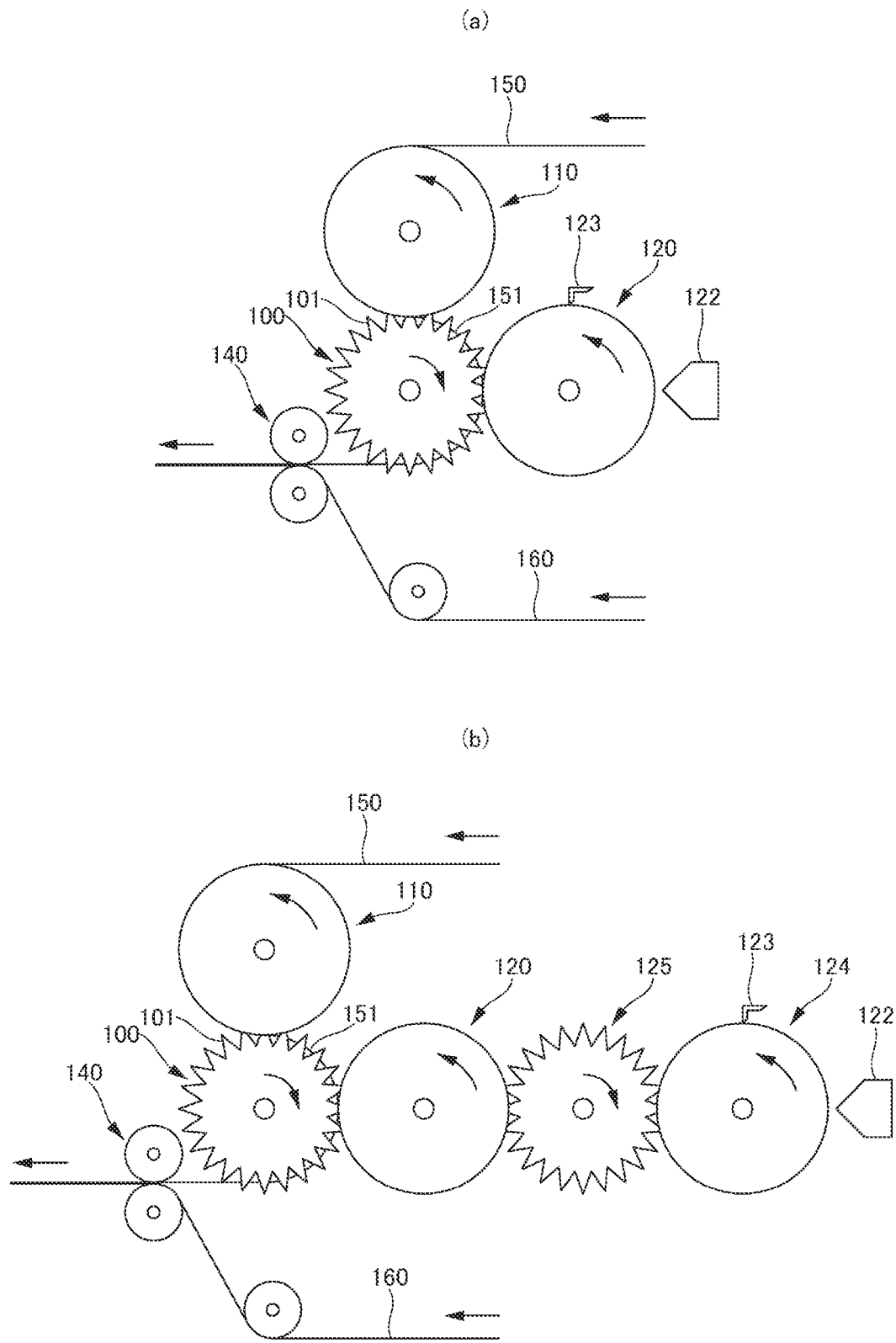
FIG. 24 is a flow diagram of equipment for bonding a perforated nonwoven fabric.

The characteristic bonding structure described above can be produced, for example, by using the perforated nonwoven fabric 151 as the cover nonwoven fabric 20 and the support sheet 160 as the liquid impervious sheet 11 in the equipment illustrated in FIG. 24. That is, this bonding equipment of the perforated nonwoven fabric is provided with a pin roll 100 having a plurality of pins 101 arranged on the circumferential surface at intervals, a concave roll 110 facing the pin roll 100 and having the concave portions 111 into which the pins 101 are inserted, and an adhesive application roll 120 facing to the pin roll 100 on the downstream side in the rotational direction of the position of the pin roll 100 facing the concave roll 110. These rolls 100, 110, and 120 are driven to rotate in a direction indicated by an arrow in the drawing such that the concave roll 110 and the adhesive application roll 120 are engaged with the pin roll 100.

Figure 25:
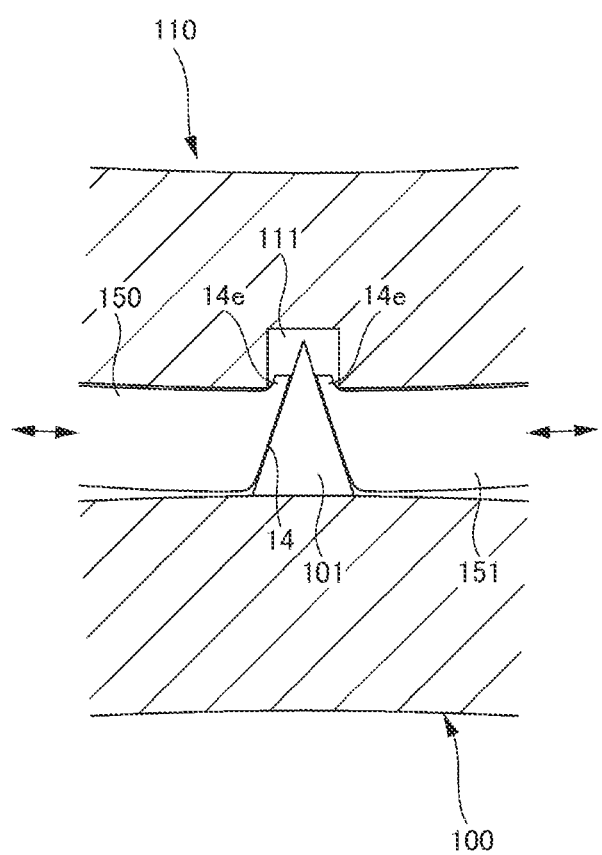
FIG. 25 is a cross-sectional view of a main part of a perforation step.

In this equipment, the perforated nonwoven fabric 151 is formed by which, firstly, a belt-like continuous nonwoven fabric 150 unwound from a raw fabric roll (not illustrated) is passed between the pin roll 100 and the concave roll 110 to pierce the pin 101 into the nonwoven fabric 150 as illustrated in FIG. 25, and a large number of holes 14 having the warped portion (burr) 14e whose peripheral portion is warped to the opposite side to the pin roll 100 side are formed in the nonwoven fabric 150 (perforation step). The nonwoven fabric 150 to be supplied is preferably a nonporous nonwoven fabric, but a perforation step may be performed by supplying a perforated nonwoven fabric.

Figure 26:
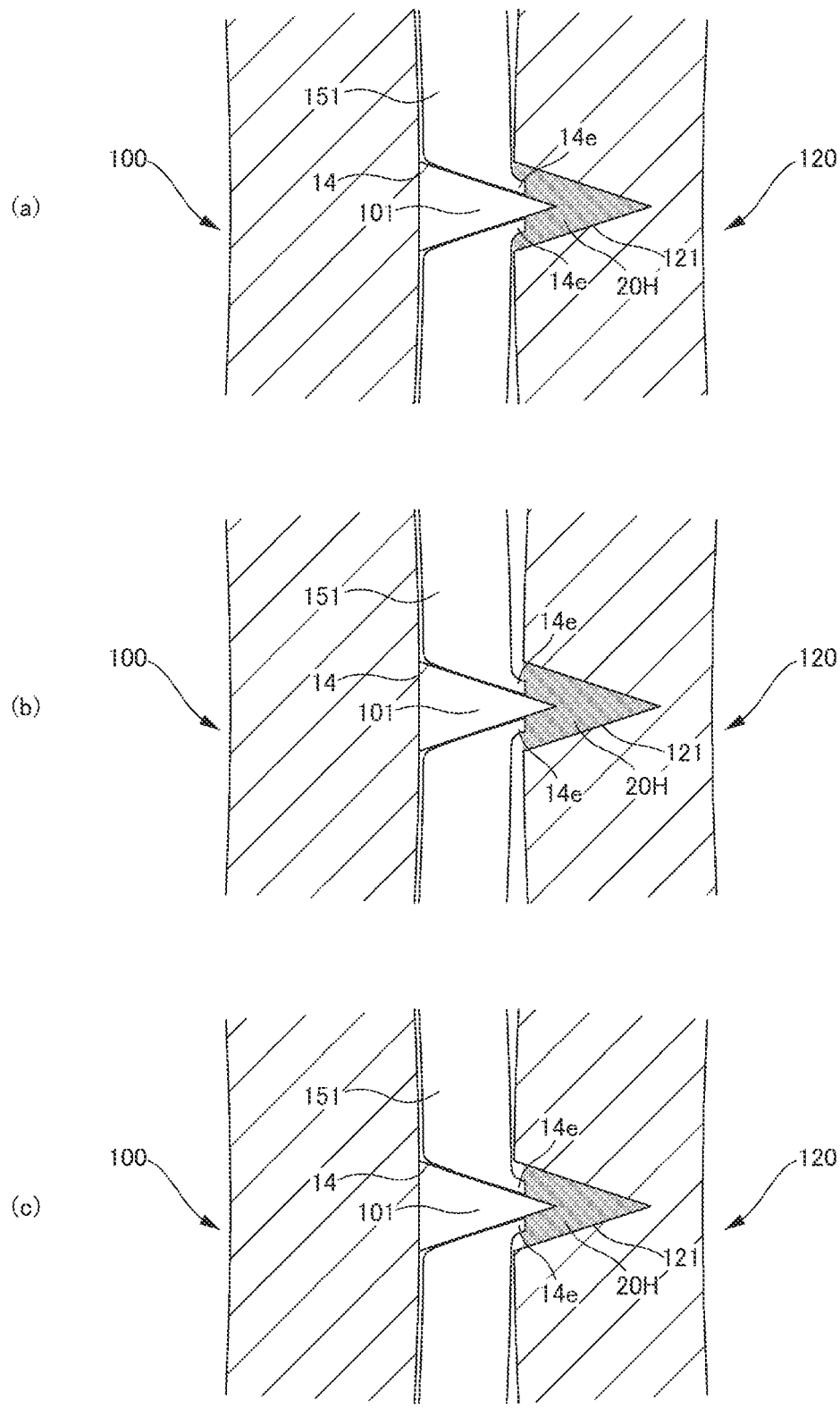
FIG. 26 is a cross-sectional view of a main part of an adhesive transfer step.

Next, the perforated nonwoven fabric 151 having the holes 14 formed in the perforation step is guided to the adhesive application roll 120 by the rotation of the pin roll 100 while maintaining the state of being pierced by the pin 101. As illustrated in various examples in FIG. 26, the hot melt adhesive 20H held on the outer peripheral surface of the adhesive application roll 120 is transferred to at least the top portion of the warped portion 14e of the perforated nonwoven fabric 151 (adhesive transfer step). It is preferable that the adhesive transfer site in the perforated nonwoven fabric 151 is only the tip portion of the warped portion 14e, but it is also possible to transfer so as to include the other portion of the warped portion 14e to obtain the above-described various adhering states.

An adhesive transfer apparatus is not particularly limited, but in the illustrated embodiment, the adhesive application roll 120 has an adhesive holding concave portion 121 into which the pin 101 and at least a tip portion of the warped portion 14e positioned around the pin are inserted. In the adhesive transfer step, after holding the hot melt adhesive 20H in the adhesive holding concave portion 121, the pin 101 and at least the tip portion of the warped portion 14e positioned around the pin 101 is inserted into the adhesive holding concave portion 121, and the hot melt adhesive 20H in the adhesive holding concave portion 121 is attached to at least the tip portion of the warped portion 14e of the perforated nonwoven fabric 151. With such an adhesive application roll 120, it is possible to reliably transfer and apply an adhesive only to at least the tip portion of the warped portion 14e of the perforated nonwoven fabric 151 while suppressing the leakage of the hot melt adhesive 20H from the hole 14. In addition, since a hot melt adhesive is generally superior to nonwoven fabric in adhesion to a plastic film, high bonding strength can be obtained by applying adhesive to the nonwoven fabric side like this.

Figure 27:
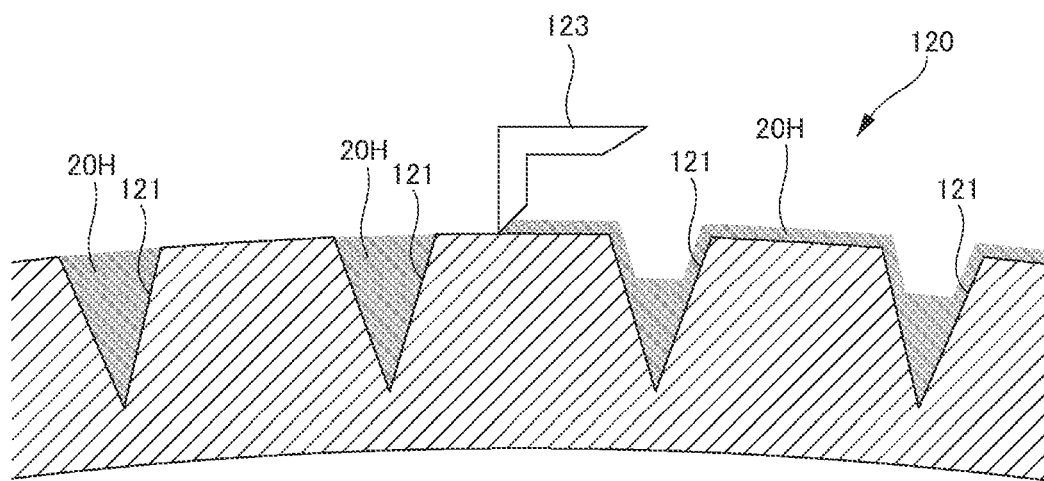
FIG. 27 is a cross-sectional view of a main part of the adhesive transfer step.
Figure 28:
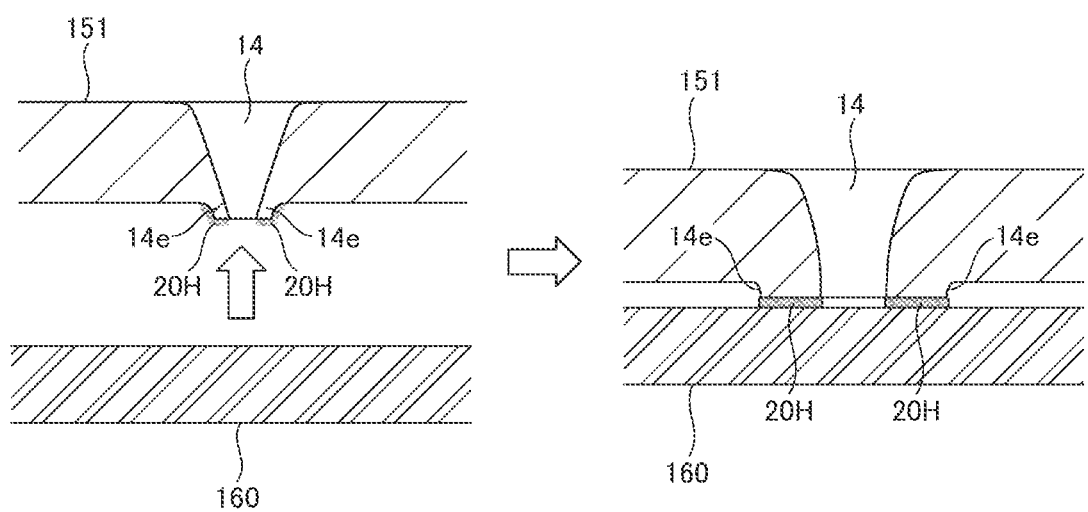
FIG. 28 is a cross-sectional view of a main part of a bonding step.

The means for holding the hot melt adhesive 20H in the adhesive holding concave portion 121 is not particularly limited. In the example illustrated in FIG. 24(a), a coating head (die) 122 and a doctor blade 123 are disposed in this order in the rotation direction so as to face the outer peripheral surface of the adhesive application roll 120, and as illustrated in FIG. 27, after a constant amount of the hot melt adhesive 20H is continuously supplied from the coating head 122 in the circumferential direction onto the outer peripheral surface of the rotating adhesive application roll 120, the hot melt adhesive 20H applied to a portion of the outer peripheral surface of the adhesive application roll 120 other than the adhesive holding concave portion 121 is scraped by the doctor blade 123 into the adhesive holding concave portion 121 and introduced into the adhesive holding concave portion 121, and the portion which does not enter the adhesive holding concave portion 121 is removed. In this way, the hot melt adhesive 20H can be substantially held only in the adhesive holding concave portion 121. As in the examples illustrated in FIGS. 24(a) and 27, in the case where the hot melt adhesive 20H fully filled in the adhesive holding concave portion 121 is held, when the clearance between a portion of the outer peripheral surface of the pin roll 100 not having the pin 101 and a portion of the outer peripheral surface of the adhesive application roll 120 not having the adhesive holding concave portion 121 is equal to or less than the thickness of the portion of the perforated nonwoven fabric 151 not having the hole 14, as illustrated in FIG. 26(a), the hot melt adhesive is widely applied not only to the whole of the warped portion 14e but also to its surroundings. On the other hand, as illustrated in FIG. 26(b), if this clearance is larger than the thickness of the portion of the perforated nonwoven fabric 151 not having the hole 14 and is equal to or smaller than the thickness of the portion of the perforated nonwoven fabric 151 having the warped portion 14e, it is possible to apply the hot melt adhesive 20H only to the tip side of the warped portion 14e.

Even when the clearance between the portion of the outer peripheral surface of the pin roll 100 not having the pin 101 and the portion of the outer peripheral surface of the adhesive application roll 120 not having the adhesive holding concave portion 121 is equal to or less than the thickness of the portion of the perforated nonwoven fabric 151 not having the hole 14, as illustrated in FIG. 26(c), by holding the hot melt adhesive 20H such that the liquid surface of the hot melt adhesive 20H in the adhesive holding concave portion 121 is lower than the above-described surface filled with the adhesive, the hot melt adhesive 20H can be applied only to the tip side of the warped portion 14e. The difference in elevation between the liquid surface of the hot melt adhesive 20H in the adhesive holding concave portion 121 and the above-described surface filled with the adhesive is not particularly limited as long as the hot melt adhesive 20H can be applied only to the tip side of the warped portion 14e, but it is preferable to be equal to or less than the warping height of the warped portion 14e.

The means for holding such a hot melt adhesive can be used in which, for example, as illustrated in FIG. 24(b), a transfer convex roll 125 facing the adhesive application roll 120 and having a large number of convex portions to be inserted into the adhesive holding concave portion 121 and a transfer concave roll 124 facing the transfer convex roll 125 and having a number of concave portions into which convex portions of the transfer convex roll 125 are inserted are provided, the coating head (die) 122 and the doctor blade 123 are disposed in this order in the rotation direction so as to face the outer peripheral surface of the transfer concave roll 124, and such that the adhesive application roll 120 and the transfer concave roll 124 are engaged with respect to the transfer convex roll 125, these rolls 120, 125, and 124 are rotationally driven in the direction indicated by the arrow in the drawing. In the example illustrated in FIG. 24(b), as in the case of the adhesive application roll 120 illustrated in FIG. 27, after the hot melt adhesive is introduced only into the concave portion of the rotating transfer concave roll 124, by inserting the convex portion of the transfer convex roll 125 into this concave portion, the hot melt adhesive in the concave portion of the transfer concave roll 124 adheres to the convex portion of the transfer convex roll 125. When the convex portion of the transfer convex roll 125 is inserted into the adhesive holding concave portion 121 of the adhesive application roll 120, the hot melt adhesive attached to the convex portion of the transfer convex roll 125 adheres to the inside of the adhesive holding concave portion 121 of the adhesive application roll 120. By interposing the transfer concave roll and the transfer convex roll as described above, all of the hot melt adhesive fully filled in the concave portion of the transfer concave roll is not supplied into the adhesive holding concave portion 121 of the adhesive application roll 120. Therefore, the liquid surface of the hot melt adhesive 20H in the adhesive holding concave portion 121 of the adhesive application roll 120 becomes lower than the above-described surface filled with the adhesive, and it becomes possible to apply the hot melt adhesive 20H only to the tip side of the warped portion 14e.

Although not illustrated, a method of holding a hot melt adhesive from the bottom of the adhesive holding concave portion 121 of the adhesive application roll 120 is also proposed as a holding means of another hot melt adhesive. In this case, by adjusting the supply amount of the hot melt adhesive, the liquid level of the hot melt adhesive 20H in the adhesive holding concave portion 121 can be freely adjusted, and it is also possible to hold the hot melt adhesive 20H so as to be lower than the above-described surface filled with the adhesive.

On the other hand, the perforated nonwoven fabric 151 to which the hot melt adhesive 20H is transferred is separated from the pin roll 100 with the rotation of the pin roll 100, and then the support sheet 160 is superimposed on the surface having the hot melt adhesive 20H, and pressed and adhered by the press roll 140 (bonding step). Such a method can form a bonding structure in which at least a tip portion of the warped portion 14e of the perforated nonwoven fabric 151 is bonded to the support sheet 160 via the hot melt adhesive 20H, and a portion other than the adhesive portion is not adhered to the support sheet 160 via the hot melt adhesive 20H.

On the other hand, in the outer member separated type underpants-type disposable diaper described above, if the total luminous transmittance of the portion of the outer member 12 overlapping with the cover nonwoven fabric 20 and not having a elastic member is 50% or more (preferably 65% or more), even in the portions concealed by the front outer member 12F and the back outer member 12B in the cover nonwoven fabric 20, it is possible to recognize that the portion having the air-permeability-improving function extends not only between the front outer member 12F and the back outer member 12B but also to both the front and back sides thereof because the hole 14 of the perforated nonwoven fabric can be visually perceived sufficiently, and the visual effect of the hole 14 is sufficiently exhibited, which is preferable. The total luminous transmittance of the outer member 12 is measured in a state where the outer sheet layer 12S and the inner sheet layer 12H are overlapped.

Further, one preferred embodiment regarding the inner and outer joined portion 201 of the outer member separated underpants-type disposable diaper described above is that, as illustrated in FIGS. 9 and 10, at least one of the front outer member 12F and the back outer member 12B is bonded to the inner member 200 in a region overlapping with both ends in the width direction of the inner member 200, and in a region between the regions overlapping with both ends in the width direction of the inner member 200, a part of the crotch side or the entire front-back direction LD is not adhered or is intermittently and peelably adhered. In this case, the gap between the inner member 200 and the outer member 12 passes to the crotch side to improve the air permeability. By turning up this portion, it is also possible to directly see the perforated cover nonwoven fabric 20 concealed by the outer member 12 such that the visual effect of the hole 14 becomes further excellent.

<Others>

In the above example, the cover nonwoven fabric 20 covering the back surface side of the liquid impervious sheet 11 is a perforated nonwoven fabric, and the present invention is applied to the bonding structure of the perforated nonwoven fabric and the liquid impervious sheet 11, but it is obvious that the bonding structure of the present invention can be applied when a perforated nonwoven fabric is also used for nonwoven fabric parts other than the cover nonwoven fabric 20. Further, it is also a preferable example that the present invention is applied to an adhering structure of a sheet on the skin side, in which the top sheet 30 is a perforated nonwoven fabric, and the intermediate sheet 40 is a supporting sheet.

<Explanation of Terms Used Herein>

The following terms in the specification have the following meanings unless otherwise specified in the specification.

"Front-back (longitudinal) direction" means a direction connecting the ventral side (front side) and the dorsal side (back side). "Width direction" means a direction orthogonal to the front-back direction (right-left direction).

"Front surface side" means a side close to the skin of a wearer wearing an underpants-type disposable diaper. "Back surface side" means a side far from the skin of a wearer wearing an underpants-type disposable diaper.

"Front surface" means a surface of a member close to the skin of a wearer wearing an underpants-type disposable diaper. "Back surface" means a surface far from the skin of a wearer wearing an underpants-type disposable diaper.

"Total luminous transmittance" means a value measured according to JIS-K 7105 for.

"Area ratio" means a ratio of an area of a target portion to a unit area, and a total area of target portions (for example, holes) in a target region (for example, a cover nonwoven fabric) is divided by the area of the target region and expressed as a percentage. In an embodiment in which a large number of target portions are provided at intervals, it is desirable to set the target region to a size such that ten or more target portions are included and obtain the area ratio. For example, the area ratio of the holes can be measured by the following procedure, for example, using the trade name VHX-1000 manufactured by KEYENCE Co., Ltd. under measurement conditions of 20 times.

(1) Set lens of 20x magnification and adjust focus. Adjust the position of a nonwoven fabric such that a hole fits 4×6.

(2) Specify the brightness of the region of the hole and measure the area of the hole.

(3) Click the color extraction of "Area measurement" in "Measurement/Comment". Click on the hole part.

(4) Click "Batch measurement", check "Show measurement result window" and save with CSV data.

"Stretch rate" means the value when the natural length is taken as 100%.

"Gel strength" is measured as follows: A super absorbent polymer 1.0 g is added to artificial urine (mixture of urea: 2 wt %, sodium chloride: 0.8 wt %, calcium chloride dihydrate: 0.03 wt %, magnesium sulfate heptahydrate: 0.08 wt %, and ion exchanged water: 97.09 wt %) 49.0 g, and stirred with a stirrer. After leaving generated gel for three hours in a thermohygrostat bath at 40° C.×60% RH, return to room temperature, and measure the gel strength with a card meter (Curdmeter-MAX ME-500, manufactured by I. techno Engineering).

"Basis weight" is measured as follows. After preliminary drying a sample or a test piece, the sample or the test piece is left in a test chamber or equipment in the standard state (the test location is at a temperature of 20±5° C. and with a relative humidity of 65% or less) to be constant weight. The preliminary drying refers to making a sample or a test piece constant weight in an environment not exceeding a temperature of 50° C. and a relative humidity of 10 to 25%. For fibers with an official moisture regain of 0.0%, preliminary drying may not be performed. A sample of dimensions of 200 mm×250 mm (±2 mm) is cut using a template for sampling (200 mm×250 mm, ±2 mm) from a test piece in a constant weight. The basis weight is set by weighing the sample, multiplying by 20, and calculating the weight per one square meter.

"Thickness" is automatically measured under the conditions of a load of 10 gf/cm$^2$ and a pressing area of 2 cm$^2$ using an automatic thickness measuring device (KES-G5 handy compression measuring program).

"Water absorption" is measured according to JIS K7223-1996 "Test method for water absorption of superabsorbent resin".

"Water absorption rate" is the "time to end point" when JIS K7224-1996 "Test method for water absorption rate of super absorbent resin" has been carried out using 2 g of superabsorbent polymer and 50 g of physiological saline solution.

"Spread state" means a flatly spread state without shrinkage or slackness.

The dimension of each part means the dimension in the spread state, not the natural length state, unless otherwise stated.

When environmental conditions in tests and measurements are not described, the tests and measurements shall be carried out in a test room or apparatus in a standard state (a temperature of 20±5° C. and a relative humidity of 65% or less at the test location).

INDUSTRIAL APPLICABILITY

The present invention can be applied to disposable wearing articles in general, such as underpants-type disposable diapers and tape-type disposable diapers, pad-type disposable diapers, disposable swimsuits, diaper covers, sanitary napkins, and the like.

REFERENCE SIGNS LIST 11 liquid impervious sheet
12 outer member
12A side seal portion
12B back outer member
12F front outer member
12H inner sheet layer
12S outer sheet layer
20 cover nonwoven fabric
20H hot melt adhesive
14 hole
14e warped portion
18 idle elastic member
200 inner member
201 inner and outer joined portion
30 top sheet
40 intermediate sheet
50 absorbent element
56 absorber
58 package sheet
60 side gather
62 gathered nonwoven fabric
100 pin roll
101 pin
111 concave
110 concave roll
120 adhesive application roll
150 nonwoven fabric
151 perforated nonwoven fabric
160 support sheet
121 adhesive holding concave portion
122 coating head
123 doctor blade
140 press roll
A1 non-elastic region
A2 elastic region
C gluteal cover portion
L intermediate region
LD front-back direction
LO leg opening
T waist region
U lower waist portion
W waist portion
WD width direction
WO waist opening

The invention claimed is:

1. A disposable wearing article, comprising: a perforated nonwoven fabric provided with a plurality of holes penetrating front and back surfaces at intervals; and a support sheet on which the perforated nonwoven fabric is bonded via a hot melt adhesive,
   wherein, in the perforated nonwoven fabric, a peripheral portion of the hole is a warped portion warped toward the support sheet side,
   at least a tip portion of the warped portion of the perforated nonwoven fabric is bonded to the support sheet via the hot melt adhesive, and
   the hot melt adhesive is not present between the perforated nonwoven fabric and the support sheet in a portion other than between the tip portion of the warped portion with an annular portion surrounding with the tip portion and the support sheet.

2. The disposable wearing article according to claim 1, wherein the hot melt adhesive is not present between the perforated nonwoven fabric and the support sheet in a portion other than between the warped portion and the support sheet.

3. The disposable wearing article according to claim 2, which comprises an absorber, a liquid impervious sheet having air permeability covering a back surface side of the absorber, and a cover nonwoven fabric covering a back surface side of the liquid impervious sheet,
   wherein the cover nonwoven fabric is the perforated nonwoven fabric, and the liquid impervious sheet is the support sheet.

4. The disposable wearing article according to claim 1, which comprises an absorber, a liquid impervious sheet having air permeability covering a back surface side of the absorber, and a cover nonwoven fabric covering a back surface side of the liquid impervious sheet,
   wherein the cover nonwoven fabric is the perforated nonwoven fabric, and the liquid impervious sheet is the support sheet.

5. A method of bonding a perforated nonwoven fabric, using a pin roll having a plurality of pins arranged at intervals on a circumferential surface, a concave roll opposed to the pin roll and having concave portions into which the pins are inserted, and an adhesive application roll opposed to the pin roll on the downstream side in the rotation direction of the pin roll from the opposed position with the concave roll,
   which comprises:
   a perforation step in which a perforated nonwoven fabric is formed by passing a nonwoven fabric between the pin roll and the concave roll to pierce the pins into the nonwoven fabric and forming a large number of holes in the nonwoven fabric having a warped portion whose peripheral portion is warped to the side opposite to the pin roll side;
   an adhesive transfer step in which while maintaining a state in which the perforated nonwoven fabric is pierced by the pins, the perforated nonwoven fabric is guided to the adhesive application roll by the rotation of the pin roll to transfer a hot melt adhesive held on an outer peripheral surface of the adhesive application roll to at least a tip portion of the warped portion in the perforated nonwoven fabric; and
   a bonding step in which the perforated nonwoven fabric onto which the hot melt adhesive is transferred is separated from the pin roll with the rotation of the pin roll and then adhered by superimposing a support sheet on a surface having the hot melt adhesive.

6. The method of bonding a perforated nonwoven fabric according to claim 5,
wherein the adhesive application roll has adhesive holding concave portions into which the pins and at least tip portions of the warped portions positioned around the pins are inserted,
in the adhesive transfer step, after holding the hot melt adhesives in the adhesive holding concave portions, the pins and at least the tip portions of the warped portions positioned around the pins are inserted into the adhesive holding concave portions, and the hot melt adhesives in the adhesive holding concave portions are applied to at least the tip portions of the warped portions of the perforated nonwoven fabric.

\* \* \* \* \*